United States Patent
Kim et al.

(10) Patent No.: US 10,493,160 B2
(45) Date of Patent: Dec. 3, 2019

(54) MICROSTRUCTURE USING CROSS-LINKED HYALURONIC ACID HYDROGEL, AND METHOD FOR PRODUCING SAME

(71) Applicant: ENDODERMA CO., LTD., Chungcheongbuk-do (KR)

(72) Inventors: Jae Soo Kim, Gyeonggi-do (KR); Soon Chang Kwon, Daejeon (KR); Sang Jin Park, Gyeonggi-do (KR)

(73) Assignee: ENDODERMA CO., LTD., Chungcheongbuk-do (KR)

( * ) Notice: Subject to any disclaimer, the term of this patent is extended or adjusted under 35 U.S.C. 154(b) by 0 days.

(21) Appl. No.: 15/550,743

(22) PCT Filed: Feb. 15, 2016

(86) PCT No.: PCT/KR2016/001463
§ 371 (c)(1),
(2) Date: Aug. 11, 2017

(87) PCT Pub. No.: WO2016/129967
PCT Pub. Date: Aug. 18, 2016

(65) Prior Publication Data
US 2018/0021437 A1    Jan. 25, 2018

(30) Foreign Application Priority Data
Feb. 13, 2015    (KR) .......... 10-2015-0022300

(51) Int. Cl.
*A61K 47/36*    (2006.01)
*A61K 9/00*    (2006.01)
(Continued)

(52) U.S. Cl.
CPC ............ *A61K 47/36* (2013.01); *A61K 9/0021* (2013.01); *B29B 13/06* (2013.01);
(Continued)

(58) Field of Classification Search
None
See application file for complete search history.

(56) References Cited

U.S. PATENT DOCUMENTS

| 4,716,224 A | 12/1987 | Sakurai et al. |
| 8,450,475 B2 | 5/2013 | Lebreton |

(Continued)

FOREIGN PATENT DOCUMENTS

| CN | 101594892 A | 12/2009 |
| CN | 102202720 A | 9/2011 |

(Continued)

OTHER PUBLICATIONS

International Search Report from corresponding PCT Application No. PCT/KR2016/001463 dated Jun. 27, 2016 and its English translation.

(Continued)

*Primary Examiner* — Bong-Sook Baek
(74) *Attorney, Agent, or Firm* — Harness, Dickey & Pierce, P.L.C.

(57) ABSTRACT

The present invention provides microstructures using cross-linked hyaluronic acid hydrogels and the method for preparing the same. The present invention for preparing microstructures using crosslinked hyaluronic acid hydrogels allows the preparation of microstructures with a uniform shape and minimum deformation. Furthermore, the microstructures made using crosslinked hyaluronic acid hydrogels in the present invention can improve skin aging, e.g. wrinkles, replenish moisture, easily absorb body fluids due to its outstanding swelling performance, provide a longer duration in the body due to its resistance against a hyaluronic acid hydrolyzing enzyme, enabling the safe delivery of effective components in the body.

16 Claims, 16 Drawing Sheets

(51) Int. Cl.
*B29B 13/06* (2006.01)
*B29C 45/00* (2006.01)
*B29C 45/40* (2006.01)
*B29K 105/00* (2006.01)

(52) U.S. Cl.
CPC .......... *B29C 45/0001* (2013.01); *B29C 45/40* (2013.01); *B29K 2105/0061* (2013.01)

(56) References Cited

U.S. PATENT DOCUMENTS

| | | | |
|---|---|---|---|
| 2006/0166928 A1 | 7/2006 | Moon et al. | |
| 2010/0316683 A1 | 12/2010 | Piron et al. | |
| 2013/0122068 A1* | 5/2013 | Fermanian | A61L 27/20 424/401 |
| 2013/0203856 A1* | 8/2013 | Cho | A61L 27/20 514/626 |
| 2013/0226235 A1 | 8/2013 | Fermanian et al. | |

FOREIGN PATENT DOCUMENTS

| | | |
|---|---|---|
| CN | 104144714 A | 11/2014 |
| JP | 2009-201956 A | 9/2009 |
| JP | 2010-511454 A | 4/2010 |
| JP | 2012-505164 | 3/2012 |
| JP | 2014-533992 A | 12/2014 |
| KR | 10-1250846 | 1/2007 |
| KR | 10-2010-0132878 | 12/2010 |
| KR | 10-1421933 | 12/2013 |
| KR | 10-2014-0101018 | 8/2014 |
| RU | 94015249 A | 4/1996 |
| WO | WO-2005/112888 | 12/2005 |
| WO | WO-2010/040271 A1 | 4/2010 |
| WO | WO-2013-055832 A1 | 4/2013 |
| WO | WO-2014/041531 A1 | 3/2014 |
| WO | WO-2014/206500 A1 | 12/2014 |

OTHER PUBLICATIONS

Notification of Reason of Refusal (Office Action) dated May 18, 2017 for corresponding Korean Patent Application No. 10-2016-0016905 with English Translation.
Office Action from corresponding Colombian Patent Application No. NC2017/0008082, dated Nov. 15, 2018.
Office Action from corresponding Russian Patent Application No. 2017130552, dated Sep. 25, 2018.
Colombian Office Action dated Jun. 14, 2018, in Colombian Patent Application No. NC2017/0008082, with English Translation.
Japanese OA issued on Jul. 19, 2018 in Japanese Patent Application No. 2017-561220, with English Translation.
Extended European Search Report of EP Patent Application No. 16749507.6 dated Aug. 27, 2018.
Office Action from corresponding Chinese Patent Application No. 201680009907.1, dated Jan. 16, 2019.
Office Action from corresponding Chinese Patent Application No. 201680009907.1, dated Jul. 8, 2019.

* cited by examiner

MICROSTRUCTURE USING CROSS-LINKED HYALURONIC ACID HYDROGEL, AND METHOD FOR PRODUCING SAME

CROSS-REFERENCE TO RELATED APPLICATIONS

This application is a national phase application of PCT Application No. PCT/KR2016/001463 filed on Feb. 15, 2016, which claims priority to Korean Patent Application No. 10-2015-0022300 filed on Feb. 13, 2015. The entire disclosures of the applications identified in this paragraph are incorporated herein by reference.

FIELD

The present patent application claims priority from Republic of Korea Patent Application No. 10-2015-0022300 filed at KIPO on Feb. 13, 2015, and the disclosed details of the patent applications are hereby incorporated by reference. The present invention relates to a biodegradable microstructure using crosslinked hyaluronic acid hydrogels and a method for preparing the same. More specifically, the invention relates to a biodegradable microstructure using hydrogels formed by cross-linking of hyaluronic acid, i.e. hyaluronic acid derivatives.

BACKGROUND

Drug delivery systems (DDS) are technologies for delivering drugs to target sites such as cells and tissues to enhance drug efficacy and reduce adverse effects by controlling drug absorption and release.

Drug delivery systems include transdermal delivery, which allows topical drug application, as well as conventional oral administration. Research has been continuously conducted to find ways to administer pharmaceutical compounds like drugs both efficiently and safely. Among them is an injection, which can be bothersome, cause pain depending on the type of patient, and has limitations for drug control besides temporary injection of drugs.

To overcome the disadvantages of an injection, research has been carried out on microstructures (microneedles), which are much smaller and cause less pain than conventional syringes. Studies are also being conducted in several areas of drug delivery, blood collection, biosensors and skin care.

Conventional microneedle production methods include U.S. Pat. No. 6,334,856 "Microneedle devices and methods of manufacture and use thereof" and Republic of Korea Patent No. 10-0793615 "Biodegradable solid microneedles and methods for preparing the same."

The aforementioned patents relate to i) the manufacture of microneedles by injecting a biodegradable viscous material into a micro-mold made from thermosetting polymer, drying and removing it from the mold (molding process) and ii) the manufacture of microneedles through the steps of coating a biodegradable viscous material to form biodegradable solid microneedles, drawing the coated biodegradable viscous material with the frame which has been patterned as a pillar, drying and cutting the drawn biodegradable viscous material (drawing process).

However, the biodegradable polymer microstructures manufactured using those conventional methods present such problems as bending and deformation during skin penetration due to their relatively low mechanical strength.

In particular, when the derivatives of polymers with high elasticity are used as a raw material, it poses limitations for the production of microstructures using the molding or drawing process, such as the inability to obtain a desired uniform shape, as well as disadvantages such as difficulty achieving the required mechanical strength of the microstructure necessary for skin penetration.

As used in the present invention, hyaluronic acid is a biodegradable polymer composed of repeating disaccharide units consisting of N-acetyl glucosamine and gluconic acid.

Microstructures manufactured using hyaluronic acid are more easily formed with lower viscosity if the average molecular weight of hyaluronic acid is lower; the higher the molecular weight of the HA, the mechanical properties and viscosity of the microstructure become higher. Such characteristics lead to the use of hyaluronic acid with low molecular weight as a common material for microstructures, but microstructures manufactured using low-molecular hyaluronic acid are prone to breaking or bending during skin penetration.

In the present invention, the inventors developed cross-linked hyaluronic acid hydrogels and the method of manufacturing microstructures using such hydrogels as a primary material in order to manufacture microstructures that use low-molecular hyaluronic acid, provide the mechanical properties appropriate for skin penetration, and are suitable for drug delivery and skin care as they easily dissolve or swell in skin.

SUMMARY OF INVENTION

Technical Problem

The inventors made research efforts to solve the problems of the conventional technologies described above. As a result of research, the inventors confirmed that a microstructure with a uniform shape and minimal deformation can be manufactured using as a primary material the hydrogels formed by crosslinked hyaluronic acid, which is a hyaluronic acid derivative and a skin component, and that the microstructure provides a high hardness and thus increases the efficiency of effective component delivery. They also confirmed that the high viscoelasticity of cross-linked hyaluronic acid used in the microstructure help improve skin tissue aging, e.g. wrinkles, and replenish moisture. The present invention was completed by further confirming that the microstructure in the present invention provides outstanding swelling performance and thus easily absorbs body fluids, that the resistance of the microstructure against the enzyme hydrolyzing hyaluronic acid increases the duration of the microstructure in the body and thus enables the stable delivery of effective components loaded on the microstructure into the body.

Accordingly, an aspect of the present invention is to provide a microstructure comprising crosslinked hyaluronic acid hydrogels.

Another aspect of the present invention is to provide a method for preparing microstructures using crosslinked hyaluronic acid hydrogels.

Other aspect of the present invention is to provide an effective component delivery system.

Other purposes and advantages of the present invention will become more obvious with the following detailed description of the invention, claims, and drawings.

Solution to Problem

In accordance with an aspect of the present invention, there is provided a microstructure containing crosslinked hyaluronic acid hydrogels.

The inventors made research efforts to solve the problems of the conventional technologies described above. As a result of research, the inventors confirmed that microstructures with a uniform shape and minimal deformation can be manufactured using as a primary material the hydrogels formed by crosslinked hyaluronic acid, which is a hyaluronic acid derivative and a skin component, and that such microstructures provide a high hardness and thus increases the efficiency of effective component delivery. They also confirmed that the high viscoelasticity of crosslinked hyaluronic acid used in the microstructure help improve skin tissue aging, e.g. wrinkles, and replenish moisture. It was further confirmed that the microstructure in the present invention provides outstanding swelling performance and thus easily absorbs body fluids, that the resistance of the microstructure against the enzyme hydrolyzing hyaluronic acid increases the duration of the microstructure in the body and thus enables the stable delivery of effective components loaded on the microstructure into the body.

As used in this specification, the term "hyaluronic acid" encompasses hyaluronic acid salts, such as hyaluronic acid sodium, hyaluronic acid potassium, hyaluronic acid magnesium, and hyaluronic acid calcium, and their mixtures, as well as hyaluronic acid.

As used in this specification, the term "hydrogel" means a three-dimensional hydrophilic polymer that retains adequate moisture. According to an object of the present invention, it means a hydrogel formed between crosslinked hyaluronans.

The present invention can provide various forms of microstructures, including microneedles, microblades, microknives, microfibers, microspikes, microprobes, microbarbs, microarrays, and microelectrodes. In one embodiment, the microstructure in the present invention refers to microneedles.

In one embodiment, crosslinked hyaluronic acid hydrogels in the present invention have crosslinking densities (crosslinking rates) ranging from 1 to 50%. In another embodiment, crosslinked hyaluronic acid hydrogels in the invention have the following crosslinking densities: 1-40%, 2-40%, 5-40%, 7-40%, 10-40%, 15-40%, 18-40%, 20-40%, 22-40%, 25-40%, 28-40%, 30-40%, 1-35%, 2-35%, 5-35%, 7-35%, 10-35%, 15-35%, 18-35%, 20-35%, 22-35%, 25-35%, 28-35%, 1-30%, 2-30%, 5-30%, 7-30%, 10-30%, 15-30%, 18-30%, 20-30%, 22-30%, 25-30%, 28-30%, 1-25%, 2-25%, 5-25%, 7-25%, 10-25%, 15-25%, 18-25%, 20-25%, 22-25%, 1-20%, 2-20%, 5-20%, 7-20%, 10-20%, 15-20%, 18-20%, 1-15%, 2-15%, 5-15%, 7-15%, 10-15%, 1-10%, 2-10%, 5-10%, 7-10%, 1-5%, 2-5%, 1-3%, and 2-3%. As demonstrated in Embodiment 6, since the enzyme that hydrolyzes hyaluronic acid in the body inhibits the biodegradation of crosslinked hyaluronic acid hydrogels, these hyaluronic acid hydrogels provide longer duration in the skin than non-crosslinked hyaluronic acid.

In one embodiment, the microstructure in the invention has a half-life of 20 to 850 hours. As used in this specification the term "half-life" means the time required for hyaluronidase, a hyaluronic acid dissolving enzyme, to break down 50% of crosslinked hyaluronic acid when the enzyme breaks down non-crosslinked hyaluronic acid 100%. As demonstrated in Embodiment 7, the microstructure in the present invention containing crosslinked hyaluronic acid hydrogels has a long half-life allowing the safe delivery of effective components in the body. If those effective components are skin care ingredients, the microstructure can provide enhanced skin care benefits.

In one embodiment, crosslinked hyaluronic acid hydrogels in the present invention are contained in the microstructure of the invention at or below 15% (w/v). In one embodiment, crosslinked hyaluronic acid hydrogels in the invention are contained in the microstructure of the invention at 0.1 to 15% (w/v). In another embodiment, crosslinked hyaluronic acid hydrogels in the invention are contained in the microstructure of the invention at 0.1-12, 0.1-10, 0.1-7.5, 0.5-12, 0.5-10, 0.5-7.5, 1-12, 1-10 or 1-7.5% (w/v).

In another embodiment, crosslinked hyaluronic acid hydrogels in the present invention are contained in the microstructure of the invention at or below 15% (w/v) if the modulus of elasticity is 0.5-5 Pa at 1 Hz, 12% (w/v) if the modulus of elasticity is 5-50 Pa, 10% (w/v) if the modulus of elasticity is 50-200 Pa, and 7.5% (w/v) if the modulus of elasticity is 200-1000 Pa. In another embodiment, crosslinked hyaluronic acid hydrogels in the present invention are contained in the microstructure of the invention at or below 15% (w/v) if the modulus of elasticity is 0.5-3 Pa at 1 Hz, 0.5-2 Pa, 1-5 Pa, 1-3 Pa, or 1-2 Pa. In another embodiment, crosslinked hyaluronic acid hydrogels in the present invention are contained in the microstructure of the invention at or below 12% (w/v) if the modulus of elasticity is 5-30 Pa at 1 Hz, 8-30 Pa, 10-30 Pa, 5-25 Pa, 8-25 Pa, 10-25 Pa, 5-20 Pa, 8-15 Pa, 20-30 Pa, or 22-26 Pa. In another embodiment, crosslinked hyaluronic acid hydrogels in the present invention are contained in the microstructure of the invention at or below 10% (w/v) if the modulus of elasticity is 50-150 Pa at 1 Hz, 50-130 Pa, 50-70 Pa, 100-150 Pa, 100-140 Pa, or 100-130 Pa. In another embodiment, crosslinked hyaluronic acid hydrogels in the present invention are contained in the microstructure of the invention at or below 7.5% (w/v) if the modulus of elasticity is 200-900 Pa at 1 Hz, 200-500 Pa, 200-300 Pa, 300-900 Pa, 400-900 Pa, 400-500 Pa, or 800-900 Pa.

Crosslinked hyaluronic acid hydrogels in the present invention can be crosslinked in any way of cross-linking hyaluronic acid as practiced in the industry. In one embodiment, crosslinked hyaluronic acid hydrogels in the present invention are hyaluronic acid hydrogels crosslinked using cross-linking agents. In another embodiment, the cross-linking agents refer to ether cross-linking agents. In one embodiment, the ether cross-linking agent means one or more selected among ethylene glycol diglycidyl ether (EGDGE) 1,4-butandiol diglycidyl ether (BDDE), 1,6-hexanediol diglycidyl ether, propylene glycol diglycidyl ether, polypropylene glycol diglycidyl ether, diglycerolpolyglycidyl ether and EDC (1-ethyl-3-(3-dimethylaminopropyl)carbodiimide). In a particular embodiment of the present invention, the ether cross-linking agent refers to 1,4-butandiol diglycidyl ether.

In one embodiment, crosslinked hyaluronic acid hydrogels in the present invention have a complex viscosity of 3-5000 Pa·s at a frequency of 0.02 Hz. In another embodiment, the complex viscosities are: 3-4500, 3-4300, 3-4200, 3-2000, 3-1500, 3-1000, 3-700, 3-650, 3-600, 3-400, 3-200, 3-150, 3-100, 3-70, 3-50, 3-20, 3-10, 3-8, 5-4500, 5-4300, 5-4200, 5-2000, 5-1500, 5-1000, 5-700, 5-650, 5-600, 5-400, 5-200, 5-150, 5-100, 5-70, 5-50, 5-20, 5-10, 50-4500, 50-4300, 50-4200, 50-2000, 50-1500, 50-1000, 50-700, 50-650, 50-600, 50-400, 50-200, 50-150, 50-100, 50-70, 100-4500, 100-4300, 100-4200, 100-2000, 100-1500, 100-1000, 100-700, 100-650, 100-600, 100-400, 100-200, 100-150, 300-4500, 300-4300, 300-4200, 300-2000, 300-1500, 300-1000, 300-700, 300-650, 300-600, 300-400, 500-4500, 500-4300, 500-4200, 500-2000, 500-1500, 500-1000, 500-700, 500-650, 500-600, 600-4500, 600-4300, 600-4200, 600-2000, 600-1500, 600-1000, 600-700, 600-650, 650-4500, 650-4300, 650-4200, 650-2000, 650-1500, 650-1000, 650-700, 650-650, 650-600, 650-400, 650-200, 650-150, 650-100, 650-70, 650-50, 650-20, 650-10, 1000-2000, 1000-1500, 1000-4500, 1000-4300, 1000-4200, 1000-2000, 1000-1500, 1300-4500, 1300-4300, 1300-4200, 1300-2000, 1300-1500, 1500-4500, 1500-4300, 1500-4200, 1500-2000, 4000-4500 or 4000-4300 Pa·s.

In one embodiment, crosslinked hyaluronic acid hydrogels in the present invention have an elastic modulus of 1-1000 Pa at a frequency of 1 Hz. In another embodiment, the elastic modulus is 1-900 Pa, 1-870 Pa or 1.5-870 Pa. In an embodiment of the invention, the elastic moduli are: 1-500, 1-450, 1-300, 1-250, 1-150, 1-130, 1-100, 1-70, 1-10, 1-5, 1-3, 8-900, 8-500, 8-450, 8-300, 8-250, 8-150, 8-130, 8-100, 8-70, 8-10, 10-900, 10-500, 10-450, 10-300, 10-250, 10-150, 10-130, 10-100, 10-70, 20-900, 20-500, 20-450, 20-300, 20-250, 20-150, 20-130, 20-100, 20-70, 50-900, 50-500, 50-450, 50-300, 50-250, 50-150, 50-130, 50-100, 50-70, 100-900, 100-500, 100-450, 100-300, 100-250, 100-150, 100-130, 110-900, 110-500, 110-450, 110-300, 110-250, 110-150, 110-130, 120-900, 120-500, 120-450, 120-300, 120-250, 120-150, 120-130, 400-900, 400-500, 400-450 or 800-900 Pa.

In one embodiment, crosslinked hyaluronic acid hydrogels in the present invention have a viscosity coefficient of 0.5-500 Pa at a frequency of 1 Hz. In another embodiment, the viscosity coefficient is 0.5-400 Pa, 0.5-300 Pa, 0.5-250 Pa or 0.7-250 Pa. In one embodiment, the viscosity coefficient is: 0.5-300, 0.5-150, 0.5-120, 0.5-70, 0.5-50, 0.5-10, 0.5-5, 0.5-3, 0.5-2, 0.5-1, 1-300, 1-150, 1-120, 1-70, 1-50, 1-10, 1-5, 1-3, 1-2, 1-1, 3-300, 3-150, 3-120, 3-70, 3-50, 3-10, 3-5, 5-300, 5-150, 5-120, 5-70, 5-50, 5-10, 6-300, 6-150, 6-120, 6-70, 6-50, 6-10, 7-500, 7-300, 7-150, 7-120, 7-70, 7-50, 7-10, 10-500, 10-300, 10-150, 10-120, 10-70, 10-50, 15-500, 15-300, 15-150, 15-120, 15-70, 15-50, 30-500, 30-300, 30-150, 30-120, 30-70, 30-50, 40-500, 40-300, 40-150, 40-120, 40-70, 40-50, 80-500, 80-300, 80-150, 80-120, 90-500, 90-300, 90-150, 90-120, 100-500, 100-300, 100-150, 100-120, 200-500, 200-300, 230-500, 230-300 or 230-250 Pa.

In one embodiment, crosslinked hyaluronic acid hydrogels in the present invention have a viscosity of 100-1000000 cp. In another embodiment, the viscosity is: 100-500000, 100-200000, 100-160000, 100-130000, 100-120000, 100-110000, 100-100000, 100-90000, 100-85000, 100-80000, 100-75000, 100-70000, 100-60000, 100-55000, 100-50000, 100-40000, 100-35000, 100-30000, 100-25000, 100-20000, 100-15000, 100-5000, 100-2000, 100-1200, 100-500, 100-400, 150-1000000, 150-500000, 150-200000, 150-160000, 150-130000, 150-120000, 150-110000, 150-100000, 150-90000, 150-85000, 150-80000, 150-75000, 150-70000, 150-60000, 150-55000, 150-50000, 150-40000, 150-35000, 150-30000, 150-25000, 150-20000, 150-15000, 150-5000, 150-2000, 150-1200, 150-500, 150-400, 500-1000000, 500-500000, 500-200000, 500-160000, 500-130000, 500-120000, 500-110000, 500-100000, 500-90000, 500-85000, 500-80000, 500-75000, 500-70000, 500-60000, 500-55000, 500-50000, 500-40000, 500-35000, 500-30000, 500-25000, 500-20000, 500-15000, 500-5000, 500-2000, 500-1200, 600-1000000, 600-500000, 600-200000, 600-160000, 600-130000, 600-120000, 600-110000, 600-100000, 600-90000, 600-85000, 600-80000, 600-75000, 600-70000, 600-60000, 600-55000, 600-50000, 600-40000, 600-35000, 600-30000, 600-25000, 600-20000, 600-15000, 600-5000, 600-2000, 600-1200, 800-1000000, 800-500000, 800-200000, 800-160000, 800-130000, 800-120000, 800-110000, 800-100000, 800-90000, 800-85000, 800-80000, 800-75000, 800-70000, 800-60000, 800-55000, 800-50000, 800-40000, 800-35000, 800-30000, 800-25000, 800-20000, 800-15000, 800-5000, 800-2000, 800-1200, 10000-1000000, 10000-500000, 10000-200000, 10000-160000, 10000-130000, 10000-120000, 10000-110000, 10000-100000, 10000-90000, 10000-85000, 10000-80000, 10000-75000, 10000-70000, 10000-60000, 10000-55000, 10000-50000, 10000-40000, 10000-35000, 10000-30000, 10000-25000, 10000-20000, 10000-15000, 25000-1000000, 25000-500000, 25000-200000, 25000-160000, 25000-130000, 25000-120000, 25000-110000, 25000-100000, 25000-90000, 25000-85000, 25000-80000, 25000-75000, 25000-70000, 25000-60000, 25000-55000, 25000-50000, 25000-40000, 25000-35000, 25000-30000, 40000-1000000, 40000-500000, 40000-200000, 40000-160000, 40000-130000, 40000-120000, 40000-110000, 40000-100000, 40000-90000, 40000-85000, 40000-80000, 40000-75000, 40000-70000, 40000-60000, 40000-55000, 40000-50000, 45000-1000000, 45000-500000, 45000-200000, 45000-160000, 45000-130000, 45000-120000, 45000-110000, 45000-100000, 45000-90000, 45000-85000, 45000-80000, 45000-75000, 45000-70000, 45000-60000, 45000-55000, 45000-50000, 50000-1000000, 50000-500000, 50000-200000, 50000-160000, 50000-130000, 50000-120000, 50000-110000, 50000-100000, 50000-90000, 50000-85000, 50000-80000, 50000-75000, 50000-70000, 50000-60000, 60000-1000000, 60000-500000, 60000-200000, 60000-160000, 60000-130000, 60000-120000, 60000-110000, 60000-100000, 60000-90000, 60000-85000, 60000-80000, 60000-75000, 60000-70000, 70000-1000000, 70000-500000, 70000-200000, 70000-160000, 70000-130000, 70000-120000, 70000-110000, 70000-100000, 70000-90000, 70000-85000, 70000-80000, 70000-75000, 100000-1000000, 100000-500000, 100000-200000, 100000-160000, 100000-130000, 100000-120000, 100000-110000, 110000-1000000, 110000-500000, 110000-200000, 110000-160000, 110000-130000, 110000-120000, 130000-1000000, 130000-500000, 130000-200000, 130000-160000, 140000-1000000, 140000-500000, 140000-200000, 140000-160000, 350000-1000000, 350000-500000, 370000-1000000, 370000-500000 or 370000-450000 cp.

In one embodiment, the microstructure in the present invention has a degree of swelling of 2000-80000%. In another embodiment, the microstructure in the present invention has the degree of swelling: 2000-75000, 2000-70000, 2000-60000, 2000-45000, 2000-40000, 2000-35000, 2000-30000, 2000-25000, 2000-15000, 2000-12000, 2000-5000, 2000-3000, 2000-2500, 2500-75000, 2500-70000, 2500-60000, 2500-45000, 2500-40000, 2500-35000, 2500-30000, 2500-25000, 2500-15000, 2500-12000, 2500-5000, 2500-3000, 3000-75000, 3000-70000, 3000-60000, 3000-45000, 3000-40000, 3000-35000, 3000-30000, 3000-25000, 3000-15000, 3000-12000, 3000-5000, 4000-75000, 4000-70000, 4000-60000, 4000-45000, 4000-40000, 4000-35000, 4000-30000, 4000-25000, 4000-15000, 4000-12000, 4000-5000, 10000-75000, 10000-70000, 10000-60000, 10000-45000, 10000-40000, 10000-35000, 10000-30000, 10000-25000, 10000-15000, 10000-12000, 20000-75000, 20000-70000, 20000-60000, 20000-45000, 20000-40000, 20000-35000, 20000-30000, 20000-25000, 25000-75000, 25000-70000, 25000-60000, 25000-45000, 25000-40000, 25000-35000, 25000-30000, 30000-75000, 30000-70000, 30000-60000, 30000-45000, 30000-40000, 30000-35000, 35000-75000, 35000-70000, 35000-60000, 35000-45000, 35000-40000, 40000-75000, 40000-70000, 40000-60000, 40000-

45000, 55000-75000, 55000-70000, 55000-60000, 65000-75000, 65000-70000, 70000-75000 or 70000-72000%. Crosslinked hyaluronic acid hydrogels in the present invention show high degrees of swelling when water is added after the drying process. By limiting the range of swelling degrees during the manufacturing of microstructures, the absorption time and the drug delivery rate of microstructures in the body can be adjusted. In particular, when crosslinked hyaluronic acid hydrogels in the present invention are used in microstructures for skin insertion, they produce great skin care results because of their outstanding swelling behavior and absorption in the body.

In one embodiment, the microstructure of the present invention further contains non-crosslinked hyaluronic acid. In an embodiment of the invention, the added non-crosslinked hyaluronic acid has 5 to 2000 parts by weight against 100 parts by weight of the hyaluronic acid hydrogel. In an embodiment of the invention, the added non-crosslinked hyaluronic acid has 7-1500, 9-1100, 10-1000, 20-500, 50-200, 5-20, 5-15 or 8-12 parts by weight against 100 parts by weight of the hyaluronic acid hydrogel. As demonstrated in Embodiment 6, the swelling degree of HA hydrogels can be adjusted by mixing non-crosslinked HA and the crosslinked HA hydrogels of the invention in a certain ratio during the manufacturing of microstructures.

In one embodiment, the microstructure of the invention includes additional effective components. In another embodiment, the effective components are drugs, skin care ingredients, or a combination of both. By containing effective components, the microstructure of the present invention can effectively deliver the effective components into the skin.

In accordance with another aspect of the present invention, there is provided a method for preparing microstructures comprising (a) the step of supplying crosslinked hyaluronic acid hydrogel into a micro-mold; (b) the step of injecting the crosslinked hyaluronic acid hydrogel into the micro-mold cavities; and (c) the step of separating the micro-mold and the crosslinked hyaluronic acid hydrogel to form a microstructure.

The detailed steps of the preparation method in the present invention are as follows:

Step (a): Supplying Crosslinked Hyaluronic Acid Hydrogel into a Micro-mold:

According to the present invention, crosslinked hyaluronic acid hydrogel is first supplied to a micro-mold.

As used in the present invention, micro-molds can be produced using any method of manufacturing micro-molds as practiced in the industry. For example, the methods of manufacturing micro-molds used in the present invention include but are not limited to: the MEMS (Micro-Electro Mechanical System) process, photolithography, biodegradable polymer microneedles: fabrication, mechanics and transdermal drug delivery (Journal of Controlled Release 104, 51-66, 2005) process, and the soft lithography process. Among them, the soft lithography process can be used in the manufacturing of elastic molds such as polydimethylsiloxane (PDMS) and poly(methyl methacrylate) (PMMA) to manufacture microstructures. The technology of manufacturing PDMS molds is a sort of plastic manufacturing technology that is used to achieve desired mold structures in various ways, such as casting, injection, and hot-embossing. For example, when a light-sensitive material is coated over a substrate such as silicon wafer and glass and a pattern is transferred using a photo mask, a master is ultimately made. Then, PDMS is cast using this as a mold and sintered to complete a PDMS mold for stamp applications.

In one embodiment, crosslinked hyaluronic acid hydrogels in the present invention have crosslinking densities from 1 to 50%. Since the microstructure of the invention and the crosslinked hyaluronic acid hydrogel thereof have in common the method for preparing microstructures, any details common to both are omitted to avoid unnecessary complexity in this specification.

Step (b): Injecting the Crosslinked Hyaluronic Acid Hydrogel into the Micro-mold Cavities Next, the crosslinked hyaluronic acid hydrogel is injected into the micro-mold cavities.

In one embodiment, injection in the present invention is carried out by applying an external force to the crosslinked hyaluronic acid hydrogel. In another embodiment of the invention, such an external force is a centrifugal force.

In another embodiment, injection in the present invention is carried out at a pressure below atmospheric pressure. In an embodiment of the invention, injection is carried out at a pressure of 100-750 mmHg. In another embodiment, injection is carried out at 100-750, 200-750, 300-750, 400-750, 500-750, 600-750, 100-700, 200-700, 300-700, 400-700, 500-700 or 600-700 mmHg. In another embodiment, the injection is carried out at a pressure below atmospheric pressure at or over 5 minutes, 5-180 minutes, 5-120 minutes, 5-60 minutes, 5-30 minutes, 5-20 minutes, 10-180 minutes, 10-120 minutes, 10-60 minutes, 10-30 minutes, 10-20 minutes, 13-180 minutes, 13-120 minutes, 13-60 minutes, 13-30 minutes, 13-20 minutes or 13-17 minutes.

In one embodiment, a step is added after the step (b), in which the crosslinked hyaluronic acid hydrogel in the present invention is supplied to the micro-mold and a primary base of a certain thickness is formed (FIG. 1). In this case, a base with the same composition as that of a microstructure can be formed and the thickness of the primary base to minimize deformation is 10 μm-200 μm or 30 μm-100 μm.

In another embodiment, a step is added after the step of forming a primary base for the present invention, in which a polymer that is different from the crosslinked hyaluronic acid hydrogel of the invention is supplied to the micro-mold and a secondary base of a certain thickness is formed (FIG. 1). In an embodiment, the secondary base of the invention contains a biocompatible polymer or adhesive. In an embodiment, the secondary base of the invention contains a biocompatible polymer or an adhesive. In a certain embodiment of the invention, the biocompatible polymer refers to one or more polymers selected among non-crosslinked hyaluronic acid (FIG. 1b), alginic acid, pectin, carrageenan, chondroitin (sulfate), dextran (sulfate), chitosan, polylysine, collagen, gellatin, carboxymethyl chitin, fibrin, agarose, pullulanpolylactide, poly(glycolide (PGA), polylactide-glycolidecopolymer (PLGA), hyaluronic acid, alginic acid, pectin, carrageenan, chondroitin (sulfate), dextran (sulfate), chitosan, polylysine, collagen, gellatin, carboxymethyl chitin, fibrin, agarose, polyanhydride, polyorthoester, polyetherester, polycaprolactone, polyesteramide, poly(butyric acid), poly(valericacid), polyurethane, polyacrylate, ethylene vinyl acetatepolymer, acrylic cellulose acetate, non-degradablepolyurethane, polystryene, polyvinylchloride, polyvinyl fluoride, poly(vinylimidazole), chlorosulphonatepolyolefins, polyethylene oxide, polyvinyl pyrrolidone (PVP), polyethylene glycol (PEG), polymethyl methacrylate, hydroxy propyl methyl cellulose (HPMC), ethyl cellulose (EC), hydroxypropyl cellulose (HPC), carboxymethylcellulose, cyclodextrin, copolymers consisting of monomers that form such polymers, and cellulose. In a certain embodiment, the adhesive refers to one or more adhesives selected among silicon, polyurethane, hyaluronic acid, physical adhesive (Gecko), polyacryl, ethyl cellulose, hydroxy methyl cellulose, ethylene vinyl acetate, and polyisobutylene.

Step (c): Separating the Micro-mold and the Crosslinked Hyaluronic Acid Hydrogel to Form a Microstructure.

Following the completion of step (b), the crosslinked hyaluronic acid hydrogel is removed from the micro-mold to form a microstructure.

In one embodiment, following the step (a), the step of drying the crosslinked hyaluronic acid hydrogels is carried out. In another embodiment, drying after the step (a) is carried out for 10 minutes to 60 hours at 15-90° C., 1-60 hours at 20-80° C., or 1-50 hours at 20-80° C. In a certain embodiment, drying after the step (a) is carried out at 10 to 30° C., for 12-60, 18-52, 24-48, 18-30, or 42-54 hours; at 40-60° C., for 1-8, 2-8, 2-6, 2.5-6, 2-3, 4-8, 4-6, 5-7 or 3-5 hours; or at 60-90° C. or 60-80° C. for 1-5, 1-3, 1.5-5, 1.5-3, 1.5-2.5, 2-4, 2-3 or 1-2 hours.

In one embodiment, following the step (b), the step of drying the crosslinked hyaluronic acid hydrogels is carried out. In another embodiment, drying after the step (b) is carried out for 10 minutes to 60 hours at 15-90° C., 10 minutes to 10 hours at 20-90° C., 10 minutes to 5 hours at 30-80° C., 10 minutes to 3 hours at 40-80° C., or 20 minutes to 2 hours at 40-80° C. In a certain embodiment, drying after the step (b) is carried out at 10 to 30° C., for 36-60 or 42-54 hours; at 40-60° C., for 0.5-7, 5-7, 0.5-2 or 0.5-1.5 hours; at 60-90° C. or 60-80° C. for 0.2-4, 2-4, 0.2-1, or 0.2-0.6 hours. The drying process after the step (b) enhances the mechanical strength of the microstructure and the flatness of the base.

In one embodiment, prior the step (a), the step of drying the crosslinked hyaluronic acid hydrogels is carried out. In another embodiment, drying prior the step (a) is carried out for 10 minutes to 60 hours at 15-90° C., 1-30 hours at 20-90° C., 1-25 hours at 20-80° C., 1.5 to 22 hours at 20-80° C. In a certain embodiment, drying prior to (a) is carried out at 10 minutes to 60 hours at 15-90° C., 10-30 hours at 15-30° C., 2-6 hours at 40-60° C., or 1-3 hours at 60-80° C. The drying of the crosslinked hyaluronic acid hydrogel carried out prior to the step (a) results in a reduction in the volume of the crosslinked HA hydrogel by 3/100 to 1/50.

In another embodiment, the drying of crosslinked hyaluronic acid hydrogels after the step (a) is carried out at a pressure below atmospheric pressure. If the drying of crosslinked hyaluronic acid hydrogels after the step (a) is carried out at atmospheric pressure of 1 (760 mmHg), the drying time can be reduced by 40% on average, ultimately enhancing the security of the effective components when the components (for instance, drug or skin care ingredients) are loaded onto the microstructure of the present invention. In a certain embodiment, the drying of crosslinked hyaluronic acid hydrogels after the step (a) is carried out at a pressure of 100-750 mmHg. In another embodiment, the drying of crosslinked hyaluronic acid hydrogels after the step (a) is carried out at 100-750, 200-750, 300-750, 400-750, 500-750, 600-750, 100-700, 200-700, 300-700, 400-700, 500-700 or 600-700 mmHg. In a certain embodiment, the drying of crosslinked hyaluronic acid hydrogels after the step (a) is carried out at a pressure below atmospheric pressure for over 5 minutes, 5-180 minutes, 5-120 minutes, 5-60 minutes, 5-30 minutes, 5-20 minutes, 10-180 minutes, 10-120 minutes, 10-60 minutes, 10-30 minutes, 10-20 minutes, 13-180 minutes, 13-120 minutes, 13-60 minutes, 13-30 minutes, 13-20 minutes or 13-17 minutes.

In one embodiment, the step of homogenizing the crosslinked hyaluronic acid hydrogels is carried out prior to the step (a). As used in this specification, the term "homogenization" means making crosslinked hyaluronic acid hydrogels to uniform particle sizes. When homogenization is carried out in the present invention, it is possible to achieve hydrogels with a smaller particle distribution and low protrusion pressure and adjust the size of crosslinked hyaluronic acid hydrogels so that it does not exceed the cavity size of microstructure molds.

In one embodiment, the method in the present invention includes the added steps (pre-a) of preparing a crosslinked hyaluronic acid hydrogel, comprising the step (i) in which a base is added to hyaluronic acid before the step (a) and the step (ii) of adding a crosslinking agent to the product of the step (i) to cause a crosslinking reaction.

In another embodiment, the average molecular weight of hyaluronic acid in the present invention is 100-5000 kDa. In a certain embodiment, the average molecular weight of hyaluronic acid in the present invention is 100-4500, 150-4500, 200-4200 kDa, 220-4200, 220-1500, 300-1500, 350-1500, 220-550, 240-490, 3000-3500, 1000-1800, 1200-1500, or 300-400 kDa.

In another embodiment, the product of the step (i) in the present invention has a concentration of 5-50% (w/v). In a certain embodiment, the product of the step (i) in the present invention has a concentration of 5-40, 5-35, 5-30, 5-25, 5-20, 5-15, 5-13, 8-40, 8-35, 8-30, 8-25, 8-20, 8-15, 8-13, 10-40, 10-35, 10-30, 10-25, 10-20, 13-40, 13-35, 13-30, 13-25, 13-20, 13-15, 15-40, 15-35, 15-30, 15-25, 15-20, 18-40, 18-35, 18-30, 18-25, 18-20, 28-40, 28-35, 28-32, or 28-30% (w/v).

In another embodiment, the product of the step (i) in the present invention has a pH of 11-13 or 12-13.

In another embodiment, the crosslinking agent used in the present invention is an ether crosslinking agent. In a certain embodiment, the crosslinking agent is 1,4-1,4-butandiol diglycidyl ether. In a certain embodiment, the crosslinking agent is added at 0.5-50 mole % of repeat units of hyaluronic acid. By adjusting the concentration of the crosslinking agent, the crosslinking density of the hyaluronic acid can be adjusted.

In another embodiment, the crosslinking reaction in the present invention takes place for 10-36 hours at 20-50° C. In a certain embodiment, the crosslinking reaction in the invention takes place for 12-36 hours at 20-30° C., 18-30 hours at 20-30° C., or 21-27 hours at 20-30° C. In a certain embodiment, the crosslinking reaction in the invention takes place 10-30 hours at 25-35° C., 15-25 hours at 25-35° C., or 18-22 hours at 25-35° C.

The crosslinked hyaluronic acid hydrogel made after the crosslinking reaction has taken place can be washed with saline solution or sodium chloride solution (NaCl) to remove any remaining BDDE or NaOH while at the same time the swelling process can be carried out. If an ethanol solution (for instance, 80% ethanol solution) is added, hydrogel particles are generated by precipitation during which any non-reactive compounds can be easily removed.

In another embodiment, the microstructure of the present invention includes an added non-crosslinked hyaluronic acid. In a certain embodiment, the added non-crosslinked hyaluronic acid has 5-2000 parts by weight against 100 parts by weight of the crosslinked hyaluronic acid hydrogel. In a certain embodiment, the added non-crosslinked hyaluronic acid has 10-1000, 7-1500, 9-1100, 20-500, 50-200, 5-20, 5-15 or 8-12 parts by weight against 100 parts by weight of the crosslinked hyaluronic acid hydrogel.

In another embodiment, bases in the present invention include and are not limited to conventional bases (for instance, NaOH) as used in the trade. In a certain embodiment, the base refers to a NaOH solution. In a certain embodiment, the base refers to 0.25N-5N NaOH solution.

Since the microstructure of the invention and the crosslinked hyaluronic acid hydrogel thereof have in common the method for preparing microstructures, any details common to both are omitted to avoid unnecessary complexity in this specification.

Beneficial Effect

The following summarizes the characteristics and advantages of the present invention:

(a) The present invention provides microstructures using crosslinked hyaluronic acid hydrogels and the method for preparing the same.

(b) The present invention for preparing microstructures using crosslinked hyaluronic acid hydrogels allows the preparation of microstructures with a uniform shape and minimum deformation.

(c) Furthermore, the microstructures made using crosslinked hyaluronic acid hydrogels in the present invention can improve skin aging, e.g. wrinkles, replenish moisture, easily absorb body fluids due to its outstanding swelling performance, provide a longer duration in the body due to its security against a hyaluronic acid dissolving enzyme, enabling the safe delivery of effective components in the body.

BRIEF DESCRIPTION OF DRAWINGS

FIG. 2 is a schematic diagram of the method for preparing microstructures in the present invention. FIG. 2a is a representative diagram of the method for preparing microstructures in the present invention, while

DETAILED DESCRIPTION

Figure 1A:
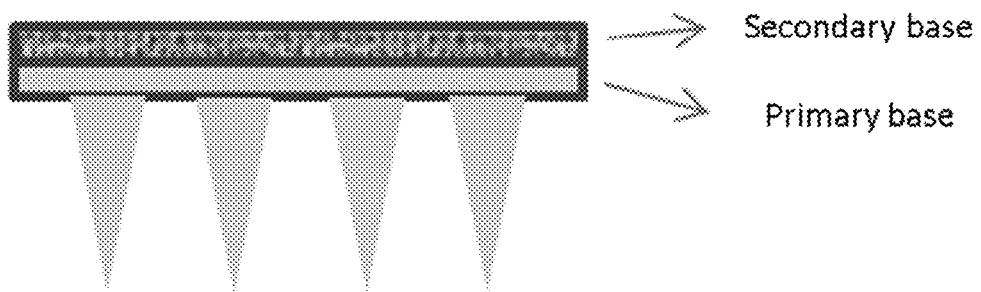
FIG. 1a is a schematic representation of the microstructure produced using cross-linked hyaluronic acid (HA) hydrogels and a method for preparing the same in the present invention.
Figure 1B:
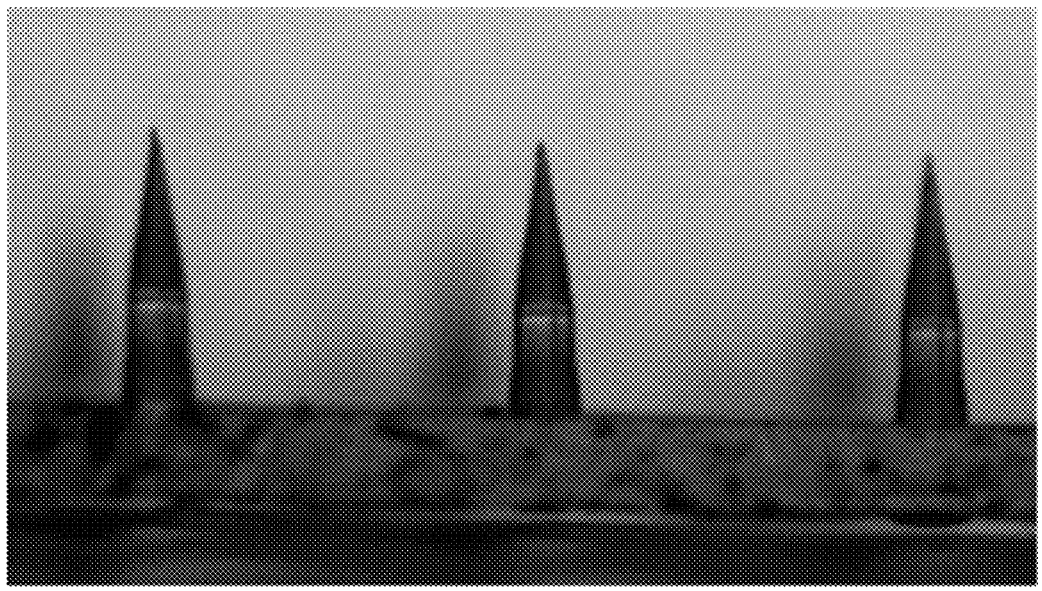
FIG. 1b shows a microscopic image of the microstructures produced according to Embodiment 3-1 of the invention. The thickness of the secondary base of the microstructures has been adjusted by adding non-cross-linked HA.
Figure 2A:
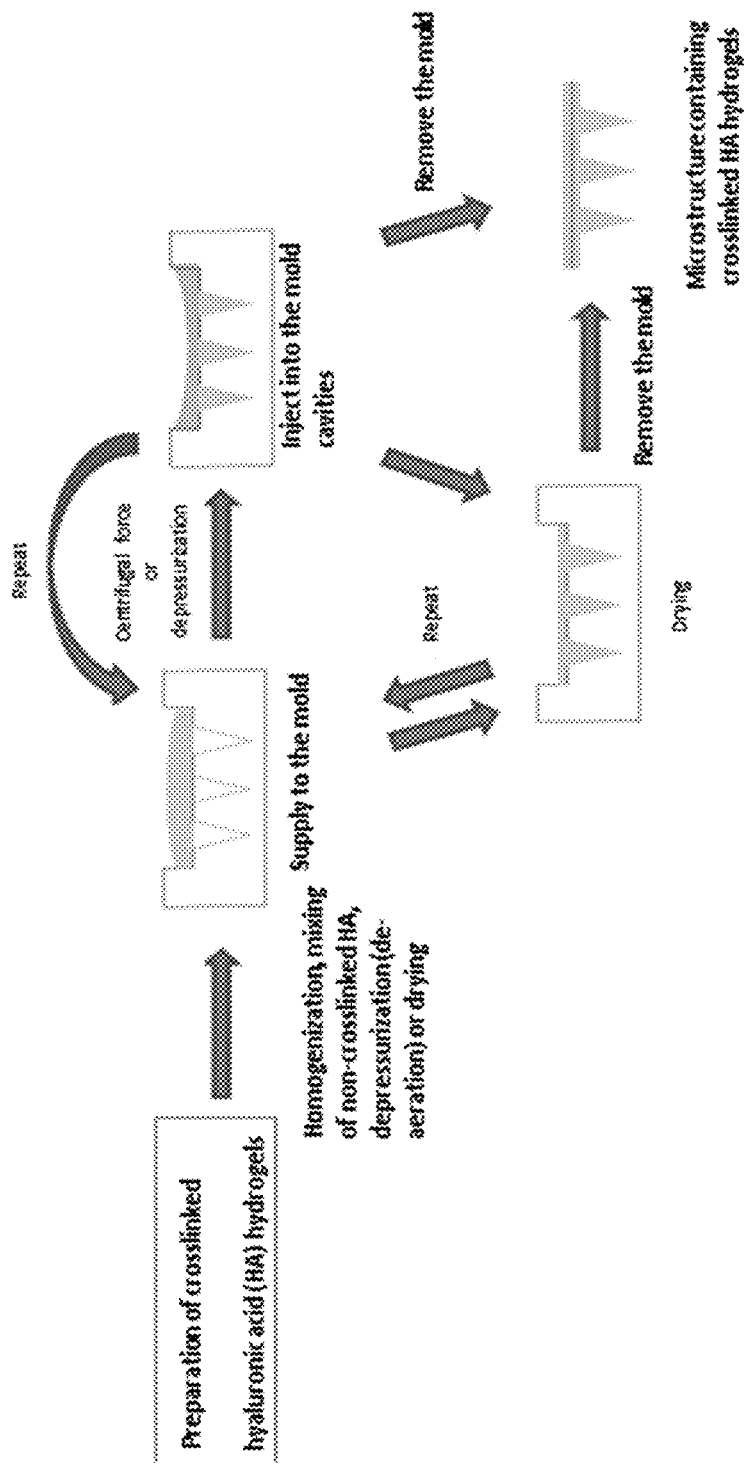
Figure 2B:
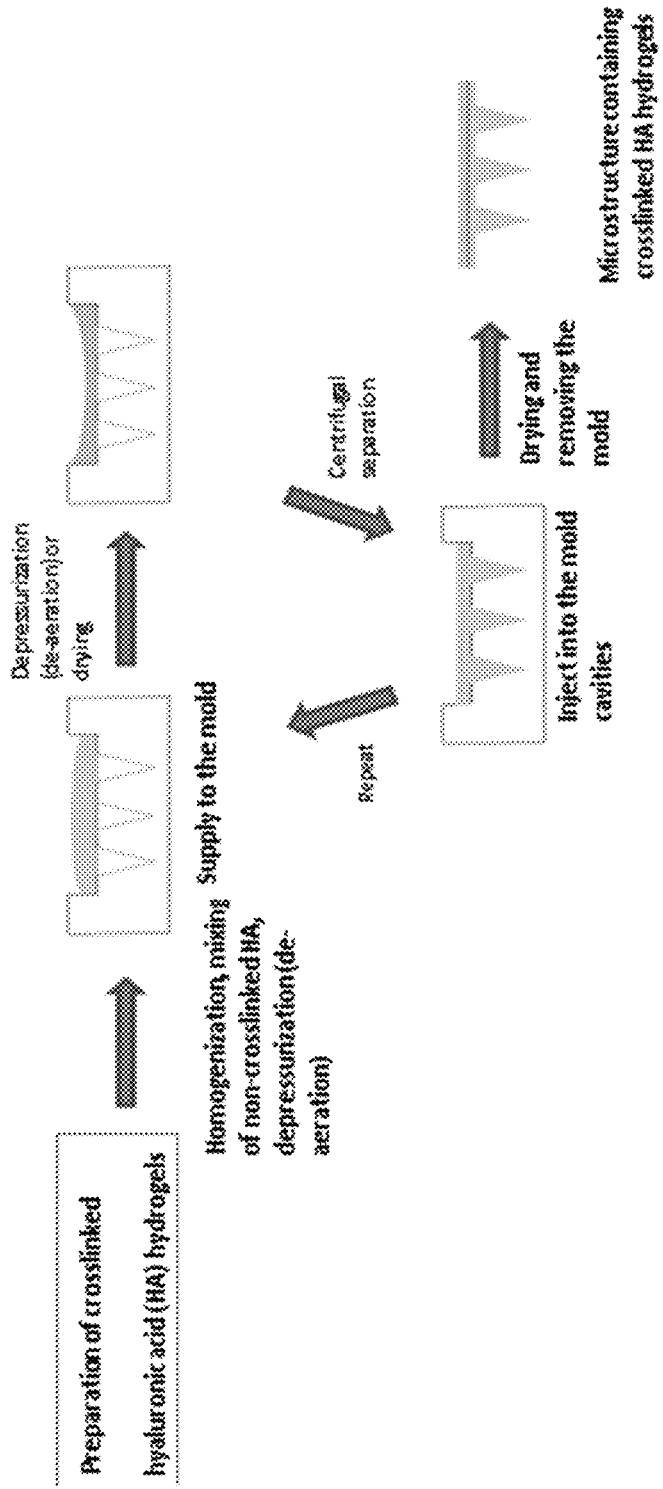
FIG. 2b is a specific diagram of Embodiment 3-2 of the invention.
Figure 3A:
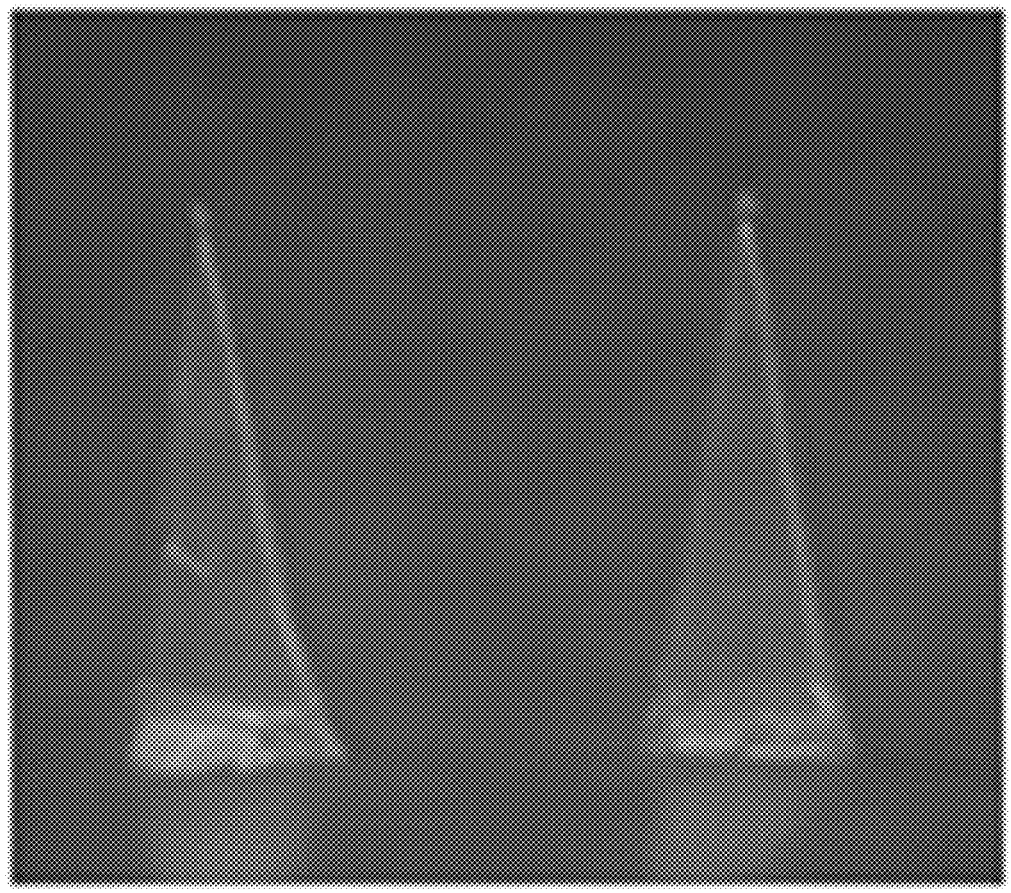
FIG. 3a shows a microscopic image (Nikon Eclipse 80i; 100×) of the microstructures produced using cross-linked hyaluronic acid hydrogels according to Embodiment 2-3 of the invention.
Figure 3B:
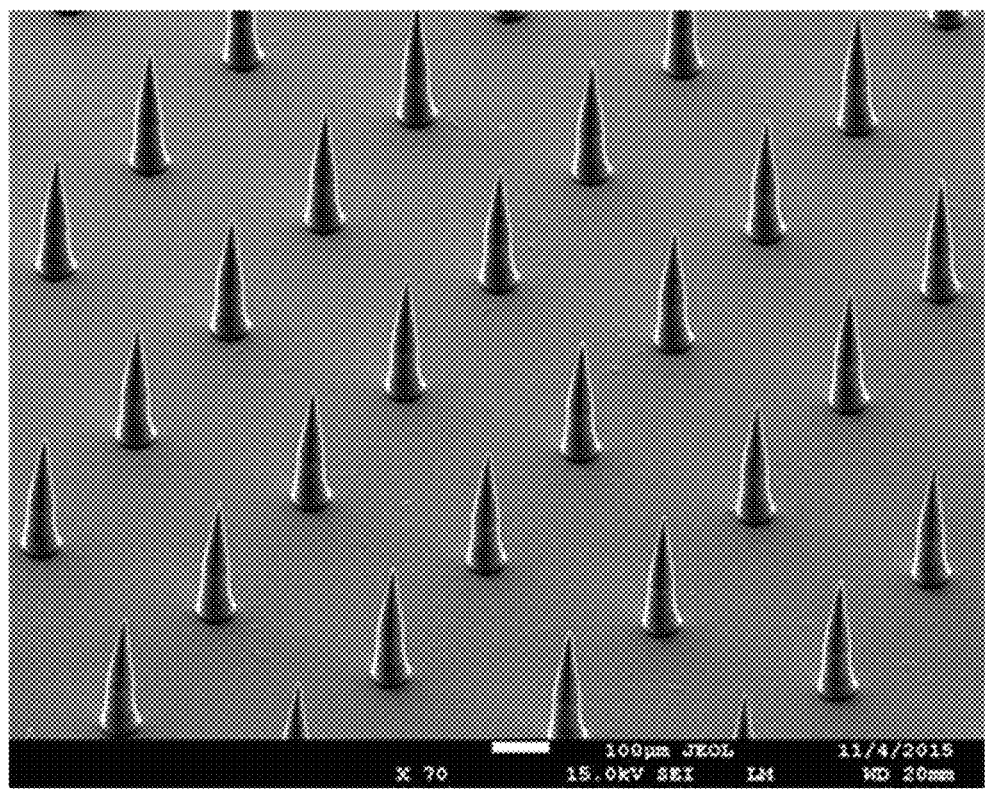
FIGS. 3b and 3c show electronic microscopic images (SEM, JEOL JSM-7500F; 70×) of the microstructures produced using cross-linked hyaluronic acid hydrogels according to Embodiment 3-2 of the invention.
Figure 3C:
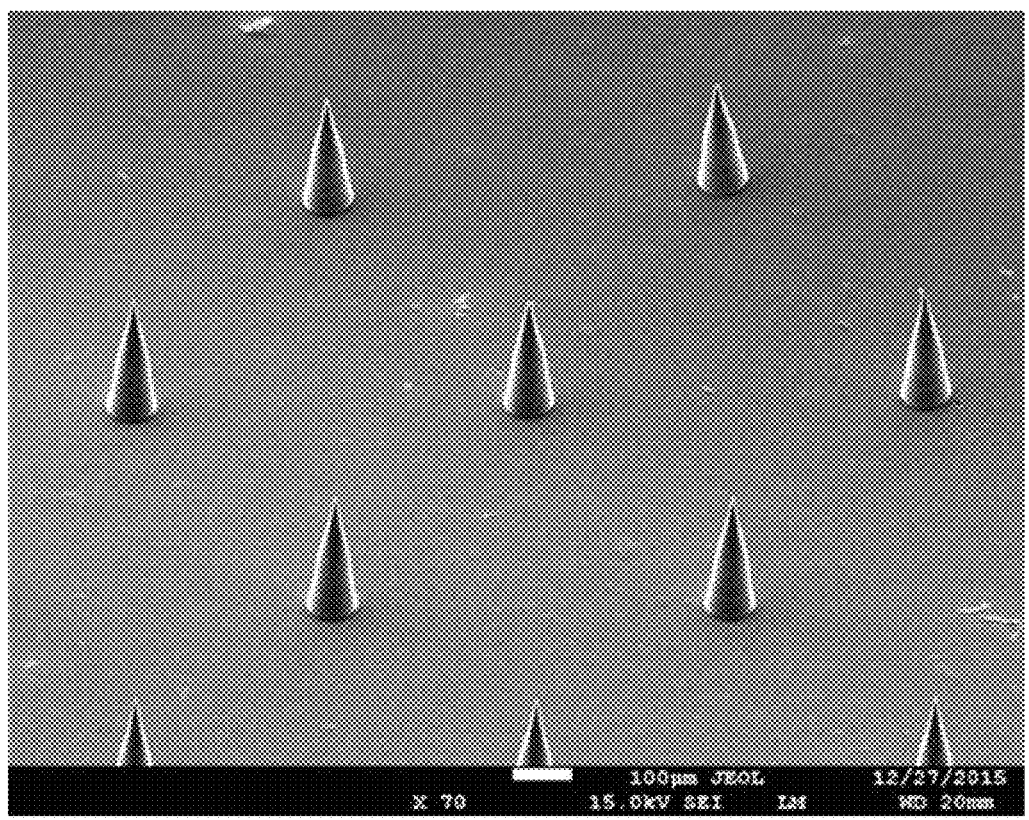

The following provides a detailed description of the present invention through examples. It is to be understood by those of ordinary skill in the art that these preferred examples are only illustrative and the claims of the present invention are not limited to such examples.

EXAMPLES

Example 1

Preparation of Crosslinked Hyaluronic Acid Hydrogel

Example 1-1

Use of 10% Hyaluronic Acid (Average Molecular Weight of 360 kDa)

Example 1-1-1

Hyaluronic acid (Bloomage Freda Biotechnology Co., Ltd., China) with an average molecular weight of 360 kDa (molecular weight range of 240-490 kDa) was completely dissolved in alkaline water (0.25 N NaOH) at a 10% concentration (w/v) and 1,4-butanediol diglycidyl ether (BDDE) was added for a crosslinking reaction with a hydroxyl group. BDDE was added at 10 mole % of HA repeat units. To complete the crosslinking reaction, the reaction took place for 24 hours at 25° C. or for 20 hours at 30° C. The hyaluronic acid solution had a pH of 12. The crosslinked hyaluronic acid hydrogel was washed with distilled water or saline solution to remove the remaining BDDE and NaOH. The crosslinking density of the crosslinked hyaluronic acid hydrogel was measured using the $H^1$-NMR analysis method (nuclear magnetic resonance spectroscopy) and the crosslinking density was 19.75%.

Example 1-1-2

A crosslinked hyaluronic acid hydrogel was prepared using the same method as Example 1-1-1, except that BDDE was added at 12 mole % of HA repeat units. The crosslinking density of the crosslinked hyaluronic acid hydrogel was 25.5%.

Example 1-1-3

A crosslinked hyaluronic acid hydrogel was prepared using the same method as Example 1-1-1, except that BDDE was added at 15 mole % of HA repeat units. The crosslinking density of the crosslinked hyaluronic acid hydrogel was 20.5%.

Example 1-1-4

BDDEA crosslinked hyaluronic acid hydrogel was prepared using the same method as Example 1-1-1, except that BDDE was added at 30 mole % of HA repeat units. The crosslinking density of the crosslinked hyaluronic acid hydrogel was 30.5%.

Example 1-1-5

A crosslinked hyaluronic acid hydrogel was prepared using the same method as Example 1-1-1, except that BDDE was added at 40 mole % of HA repeat units. The crosslinking density of the crosslinked hyaluronic acid hydrogel was 31.75%.

Example 1-2

Use of 15% Hyaluronic Acid (Average Molecular Weight of 360 kDa)

Example 1-2-1

Hyaluronic acid (Bloomage Freda Biotechnology Co., Ltd., China) with an average molecular weight of 360 kDa (molecular weight range of 240-490 kDa) was completely dissolved in alkaline water (0.25 N NaOH) at a 15% concentration (w/v) and BDDE was added for a crosslinking reaction with a hydroxyl group. To complete the crosslinking reaction, the reaction took place for 24 hours at 25° C. or for 20 hours at 30° C. The hyaluronic acid solution had a pH of 12. The crosslinked hyaluronic acid hydrogel was washed with distilled water or saline solution to remove the remaining BDDE and NaOH. The crosslinking density of the crosslinked hyaluronic acid hydrogel was 9.25%.

Example 1-2-2

A crosslinked hyaluronic acid hydrogel was prepared using the same method as Example 1-2-1, except that BDDE was added at 7.5 mole % of HA repeat units. The crosslinking density of the crosslinked hyaluronic acid hydrogel was 19.75%.

Example 1-3

Use of 20% Hyaluronic Acid (Average Molecular Weight of 360 kDa)

Hyaluronic acid (Bloomage Freda Biotechnology Co., Ltd., China) with an average molecular weight of 360 kDa (molecular weight range of 240-490 kDa) was completely dissolved in alkaline water (0.25 N NaOH) at a 20% concentration (w/v) and BDDE was added for a crosslinking reaction with a hydroxyl group. BDDE was added at 3 mole % of HA repeat units. To complete the crosslinking reaction, the reaction took place for 24 hours at 25° C. or for 20 hours at 30° C. The hyaluronic acid solution had a pH of 12. The crosslinked hyaluronic acid hydrogel was washed with distilled water or saline solution to remove the remaining BDDE and NaOH. The crosslinking density of the crosslinked hyaluronic acid hydrogel was 6.25%.

Example 1-4

Use of 30% Hyaluronic Acid (Average Molecular Weight of 360 kDa

Hyaluronic acid (Bloomage Freda Biotechnology Co., Ltd., China) with an average molecular weight of 360 kDa (molecular weight range of 240-490 kDa) was completely dissolved in alkaline water (0.25 N NaOH) at a 30% concentration (w/v) and BDDE was added for a crosslinking reaction with a hydroxyl group. BDDE was added at 1 mole % of HA repeat units. To complete the crosslinking reaction, the reaction took place for 24 hours at 25° C. or for 20 hours at 30° C. The hyaluronic acid solution had a pH of 12. The crosslinked hyaluronic acid hydrogel was washed with distilled water or saline solution to remove the remaining BDDE and NaOH. The crosslinking density of the crosslinked hyaluronic acid hydrogel was 2.25%.

Example 1-5

Use of 10% Hyaluronic Acid (Average Molecular Weight of 1,400 kDa)

Example 1-5-1

Hyaluronic acid (Bloomage Freda Biotechnology Co., Ltd., China) with an average molecular weight of 1,400 kDa (molecular weight range of 1000-1800 kDa) was completely dissolved in alkaline water (0.25 N NaOH) at a 10% concentration (w/v) and BDDE was added for a crosslinking reaction with a hydroxyl group. BDDE was added at 12 mole % of HA repeat units. To complete the crosslinking reaction, the reaction took place for 24 hours at 25° C. or for 20 hours at 30° C. The hyaluronic acid solution had a pH of 12. The crosslinked hyaluronic acid hydrogel was washed with distilled water or saline solution to remove the remaining BDDE and NaOH. The crosslinking density of the crosslinked hyaluronic acid hydrogel was 21.25%.

Example 1-5-2

A crosslinked hyaluronic acid hydrogel was prepared using the same method as Example 1-5-1, except that BDDE was added at 20 mole % of HA repeat units. The crosslinking density of the crosslinked hyaluronic acid hydrogel was 26.75%.

Example 1-6

Use of 20% Hyaluronic Acid (Average Molecular Weight of 3,200 kDa)

Hyaluronic acid (Bloomage Freda Biotechnology Co., Ltd., China) with an average molecular weight of 3,200 kDa (molecular weight range of 2400-4000 kDa, CPN, Czech Republic) was completely dissolved in alkaline water (0.25 N NaOH) at a 20% concentration (w/v) and BDDE was added for a crosslinking reaction with a hydroxyl group. BDDE was added at 5 mole % of HA repeat units. To complete the crosslinking reaction, the reaction took place for 24 hours at 25° C. or for 20 hours at 30° C. The hyaluronic acid solution had a pH of 12. The crosslinked hyaluronic acid hydrogel was washed with distilled water or saline solution to remove the remaining BDDE and NaOH. The crosslinking density of the crosslinked hyaluronic acid hydrogel was 7.75%.

Example 1-7

Use of 30% Hyaluronic Acid (Average Molecular Weight of 3,200 kDa)

Hyaluronic acid with an average molecular weight of 3,200 kDa (molecular weight range of 2400-4000 kDa) was completely dissolved in alkaline water (0.25 N NaOH) at a 30% concentration (w/v) and BDDE was added for a crosslinking reaction with a hydroxyl group. BDDE was added at 1 mole % of HA repeat units. To complete the crosslinking reaction, the reaction took place for 24 hours at 25° C. or for 20 hours at 30° C. The hyaluronic acid solution had a pH of 12. The crosslinked hyaluronic acid hydrogel was washed with distilled water or saline solution to remove the remaining BDDE and NaOH. The crosslinking density of the crosslinked hyaluronic acid hydrogel was 2.25%.

Example 2

Preparation of Microstructure Using Crosslinked Hyaluronic Acid Hydrogel in the Present Invention Preparation of PDMS Micro-mold A positive master mold was manufactured on a silicon wafer using the MEMS (Micro-Electro Mechanical System) process and then a thermosetting silicone (polydimethylsilozane; PDMS) was used to manufacture a negative mold from the positive master mold.

Example 2-1

PDMS The crosslinked hyaluronic acid hydrogel prepared using the method of Example 1 was supplied into the PDMS micro-mold and dried for 48 hours at room temperature (25° C.), six hours at 50° C., or three hours at 70° C. Then the hydrogel was injected into the mold cavities and the mold was removed to manufacture a crosslinked hyaluronic acid hydrogel microstructure.

Example 2-2

The crosslinked hyaluronic acid hydrogel prepared using the method of Example 1 was supplied into the PDMS micro-mold and injected into the cavities of the mold under the condition of depressurization (650 mmHg, 15 minutes). Then it was dried for 48 hours at room temperature (25° C.), six hours at 50° C., or three hours at 70° C., and the mold was removed to manufacture a crosslinked hyaluronic acid hydrogel microstructure.

Example 2-3

The crosslinked hyaluronic acid hydrogel prepared using the method of Example 1 was supplied into the PDMS micro-mold and injected into the cavities of the mold using a centrifuge at 900 g for 15 minutes. Then it was dried for 48 hours at room temperature (25° C.), six hours at 50° C., or three hours at 70° C., and the mold was removed to manufacture a crosslinked hyaluronic acid hydrogel microstructure.

Example 2-4

100 ml of the crosslinked hyaluronic acid hydrogel prepared using the method of Example 1 was dried for 20 hours at room temperature, four hours at 50° C., or two hours at 70° C., until the hydrogel became 3 ml or 10 ml. After the hydrogel was supplied into the PDMS micro-mold and injected into the cavities of the mold using a centrifuge at 900 g for 60 minutes. Then, the mold was removed to prepare a crosslinked hyaluronic acid hydrogel microstructure.

Example 2-5

The crosslinked hyaluronic acid hydrogel prepared using the method of Example 1 was supplied into the in the PDMS micro-mold after being homogenized using a homogenizer (Primix Corporation, Japan) at 8,000 rpm for 10 minutes. Then it was dried for 24 hours at room temperature, five hours at 50° C., or 2.5 hours at 70° C., and evenly injected into the cavities of the mold using a centrifuge at 900 g for 20 minutes. Then, the mold was removed to prepare a crosslinked hyaluronic acid hydrogel microstructure. The intermediate drying process helps enhance the mechanical strength of the microstructure and the flatness of the base.

Example 2-6

The crosslinked hyaluronic acid hydrogel prepared using the method of Example 1 was supplied into the in the PDMS micro-mold after being homogenized using the homogenizer at 8,000 rpm for 10 minutes. Then it was dried for 12 hours at 37° C., four hours at 50° C., or 2.5 hours at 70° C., and evenly injected into the cavities of the mold using a centrifuge at 900 g for 20 minutes. It was further dried for an hour at 50° C. or 30 minutes at 70° C. Then, the mold was removed to prepare a crosslinked hyaluronic acid hydrogel microstructure. The additional drying process helps enhance the mechanical strength of the microstructure by further removing the remaining moisture.

Example 2-7

The crosslinked hyaluronic acid hydrogel prepared using the method of Example 1 was supplied into the in the micro-mold after being homogenized using the homogenizer at 8,000 rpm for 10 minutes. Then it was dried for seven hours at 37° C., 2.5 hours at 50° C., or 1.5 hours at 70° C. under the depressurization condition (684 mmHg), and evenly injected into the cavities of the mold using a centrifuge at 900 g for 20 minutes. It was further dried for an hour at 50° C. or 30 minutes at 70° C. Then, the mold was removed to prepare a crosslinked hyaluronic acid hydrogel microstructure. The depressurized drying process facilitates the mold injection of derivative material, shortens the intermediate drying time (by 40% on average), and enhances stability when a drug is loaded onto the microstructure.

Comparative Example 1

Preparation of Microstructure Using Only Unmodified (Non-crosslinked) Hyaluronic Acid 30% (w/v) non-crosslinked hyaluronic acid was supplied into the PDMS micro-mold and injected into the cavities of the mold using a centrifuge for 15 minutes at 900 g. Then, it was dried for 30 minutes at room temperature (25° C.) and the mold was removed to prepare a microstructure.

Example 3

Preparation of Microstructure Using Crosslinked Hyaluronic Acid Hydrogel and Unmodified (Non-crosslinked) Hyaluronic Acid Hydrogel Example 3-1

The crosslinked hyaluronic acid hydrogel in Example 1 was homogenized using a homogenizer at 8,000 rpm for 10 minutes. Then the crosslinked hyaluronic acid hydrogel was mixed with non-crosslinked hyaluronic acid at a weight ratio of 1:1, 1:5, 1:10, or 5:1. Bubbles were completely removed through a de-aeration process using a vacuum pump (750 mmHg) before the hydrogel was supplied into the micromold. The hydrogel was injected into the cavities of the mold under the depressurization condition (650 mmHg, 15 minutes), dried for 48 hours at room temperature (25° C.), six hours at 50° C. or 3 hours at 70° C. Then, the mold was removed to prepare a microstructure using crosslinked hyaluronic acid hydrogel and non-crosslinked hyaluronic acid.

Example 3-2

The crosslinked hyaluronic acid hydrogel in Example 1 was homogenized using a homogenizer at 8,000 rpm for 10 minutes. Then the crosslinked hyaluronic acid hydrogel was mixed with non-crosslinked hyaluronic acid at a weight ratio of 1:1, 1:5, 1:10, or 5:1. The hydrogel was supplied into the micro-mold under the depressurization condition (250 mmHg, bubbles removed) and bubbles were completely removed through an additional de-aeration process using a vacuum pump (750 mmHg, 15 minutes). The hydrogel was dried for 12 hours at 37° C., four hours at 50° C. or 2.5 hours at 70° C. and evenly injected into the cavities of the mold using a centrifuge for 20 minutes at 900 g. Then it was further dried for an hour at 50° C. or 30 minutes at 70° C. Then, the mold was removed to prepare a microstructure using crosslinked hyaluronic acid hydrogel and non-crosslinked hyaluronic acid.

Example 4

Viscoelasticity of Crosslinked Hyaluronic Acid Hydrogel

Crosslinked hyaluronic acid hydrogels have various viscoelasticities, depending on the crosslinking method and the amount of crosslinking agent added. If the hydrogel has an excessively high viscosity (over 2,500,000 cp) or excessively high elastic modulus (over 100 kPa when measured at 1 Hz), it is impossible to prepare a microstructure with a desired shape and hardness.

This embodiment was implemented to verify the conditions for microstructure preparation by the viscoelasticity of crosslinked hyaluronic acid hydrogel in the present invention. During the preparation of microstructure based on the viscoelasticity of crosslinked hyaluronic acid hydrogel, the drying time and centrifugal conditions can be adjusted. If the elastic modulus measured at 1 Hz is greater than 100 Pa or the average particle size of the gel is over 200 μm or heterogeneous, the homogenization process of hydrogel particles is required.

To verify the viscoelasticity of the crosslinked hyaluronic acid hydrogel prepared in the present invention, the complex viscosities (|n*|, Pa·s), elastic moduli (G', Pa) and viscosity coefficients (G'', Pa) of the products of Embodiment 1-1 through 1-5 were measured.

Using the AR 2000EX rheometer (T.A Instruments Ltd., USA), 4-cm, 2°-cone and plate geometry, the measurements were taken in 1% strain and oscillation mode at 0.02 to 1 Hz. Table 1 shows the complex viscosities measured at 0.02 Hz and the elastic moduli and viscosity coefficients measured at 1 Hz. The deviation of the equipment was ±10%, and the test was performed at 25° C.

TABLE 1

|  | HA Molecular weight (kDa) | Amount of crosslinking agent added (mole % per HA repeat unit) | Complex viscosity (\|n*\|) (Pa · s at 0.02 Hz) | Elastic modulus (G') (Pa at 1 Hz) | Viscosity coefficient (G'') (Pa at 1 Hz) | Maximum content of crosslinked HA hydrogel that can be contained in microstructure (%, w/v) |
|---|---|---|---|---|---|---|
| Example 1-1-1 | 360 | 10 | 6.91 | 1.58 | 0.85 | 15% |
| Example 1-1-2 | 360 | 12 | 67.00 | 10.54 | 5.18 | 12% |
| Example 1-1-3 | 360 | 15 | 64.39 | 12.02 | 1.52 | 12% |
| Example 1-1-4 | 360 | 30 | 1754.33 | 435.50 | 100.16 | 7.5% |
| Example 1-1-5 | 360 | 40 | 4154.67 | 860.47 | 246.53 | 7.5% |
| Example 1-2-1 | 360 | 5 | 570.01 | 119.50 | 4.72 | 10% |
| Example 1-2-2 | 360 | 7.5 | 389.26 | 61.50 | 6.09 | 10% |
| Example 1-3 | 360 | 3 | 678.80 | 119.76 | 17.66 | 10% |
| Example 1-4 | 360 | 1 | 600.05 | 129.56 | 112 | 10% |
| Example 1-5-1 | 1,400 | 12 | 138.47 | 24.16 | 7.52 | 12% |
| Example 1-5-2 | 1,400 | 20 | 1469.67 | 227.35 | 45.95 | 7.5% |

As shown in Table 1, the complex viscosity and elastic modulus of the crosslinked hyaluronic acid hydrogel were affected by the HA molecular weight and the ratio of crosslinking agent.

It was confirmed that, when the initial reactive concentration of hyaluronic acid is 10% (w/v), the complex viscosity and elastic modulus of the crosslinked hyaluronic acid hydrogel increase as the amount of crosslinking agent added increases. Meanwhile, if the initial reactive concentration of HA increases, even if the amount of crosslinking agent added is small, it exhibits relatively high complex viscosity and elastic modulus.

Figure 4:
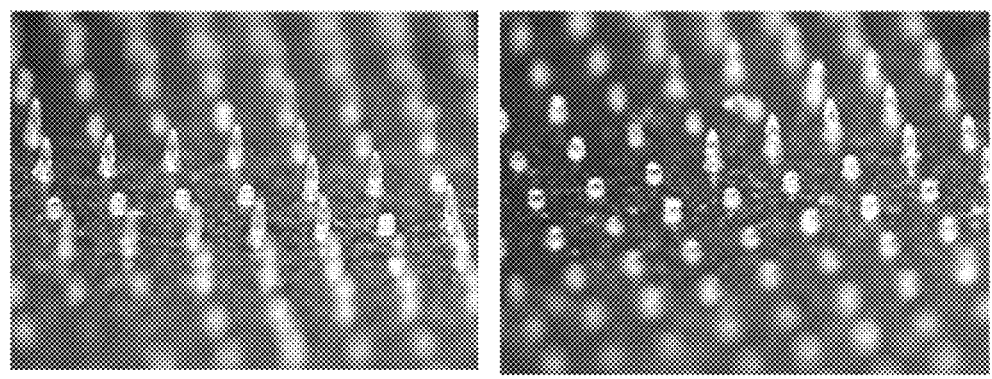
FIG. 4 shows microscopic images (Nikon Eclipse 80i; 40×) of crosslinked hyaluronic acid hydrogels when they are contained in the microstructures exceeding the maximum content scope.

Furthermore, after the products of Examples 1-1 through 1-5 were dried before being supplied into the mold as described in Example 2-4, the inventors measured the maximum levels of crosslinked hyaluronic acid hydrogel that could be contained to the extent that the preparation of microstructure was possible by varying the concentrations. Table 1 shows the measurements. It was confirmed that, when the crosslinked hyaluronic acid hydrogel alone exceeds the maximum content during microstructure preparation, the high elasticity (or restoring force) made mold injection difficult. More specifically, if the solid content in the crosslinked hyaluronic acid hydrogel in Example 1-1-2 was set to 15% and prepared as described in Example 2-4, the microstructure was dried in heterogeneous shape and the amount injected in the mold varied across structures, resulting in the preparation of microstructures with heterogeneous lengths (FIG. 4).

Example 5

Measurement of the Viscosity Range of Homogenized Crosslinked Hyaluronic Acid Hydrogel To verify the viscosity range of the crosslinked hyaluronic acid hydrogel prepared in Example 1, the products of Examples 1-1 through 1-5 were homogenized using a crusher (homogenizer or plunger mill) and their viscosities were measured using a viscometer (Brookfield DV-I prime).

The homogenized crosslinked hyaluronic acid hydrogels were transferred to beakers while carefully avoiding the formation of bubbles. They were left unattended at room temperature for 2-3 hours until the temperature of the entire sample became uniform. Then, the beakers were anchored on a flat ground, the RPMs were adjusted using LV62 or 64 spindle until the torque reached the 10-100% range. Three minutes after the measurement began, the stabilized viscosities were read and the viscosities of the homogenized crosslinked hyaluronic acid hydrogels were measured. Table 2 shows the viscosity range.

TABLE 2

| | Amount of crosslinking agent added (mole % per HA repeat unit) | Spindle No. | RPM | Torque (%) | Viscosity (cp) |
|---|---|---|---|---|---|
| Example 1-1-1 | 10 | 63 | 1.0 | 90-100 | 112000-120000 |
| | | 64 | 5.0 | 30-40 | 380000-445000 |
| Example 1-1-2 | 12 | 63 | 60.0 | 10-20 | 300-450 |
| | | 63 | 100.0 | 15-25 | 180-300 |
| Example 1-1-3 | 15 | 63 | 60.0 | 30-40 | 300-450 |
| | | 63 | 100.0 | 15-25 | 700-1150 |
| Example 1-1-4 | 30 | 63 | 2.0 | 80-90 | 50000-53000 |
| | | 63 | 2.5 | 90-100 | 45000-51000 |
| Example 1-1-5 | 40 | 63 | 1.0 | 90-100 | 110000-120000 |
| | | 64 | 5.0 | 50-60 | 63000-72000 |
| Example 1-2-1 | 5 | 63 | 1.0 | 60-70 | 101000-107000 |
| | | 64 | 5.0 | 60-70 | 72000-82000 |
| Example 1-2-2 | 7.5 | 63 | 2.5 | 70-80 | 37000-38000 |
| | | 63 | 5.0 | 90-100 | 27000-33000 |
| Example 1-3 | 3 | 63 | 1.5 | 65-75 | 48000-66000 |
| | | 63 | 6.0 | 71-93 | 14000-19000 |
| Example 1-4 | 1 | 62 | 1.5 | 60-70 | 12000-18000 |
| | | 63 | 5.0 | 60-70 | 14000-21000 |
| Example 1-5-1 | 12 | 63 | 5.0 | 60-65 | 140000-155000 |
| | | 63 | 10 | 80-90 | 9100-11000 |
| Example 1-5-2 | 20 | 63 | 0.5 | 50-60 | 112000-152000 |
| | | 64 | 5.0 | 35-45 | 43000-53000 |

Figure 5A:
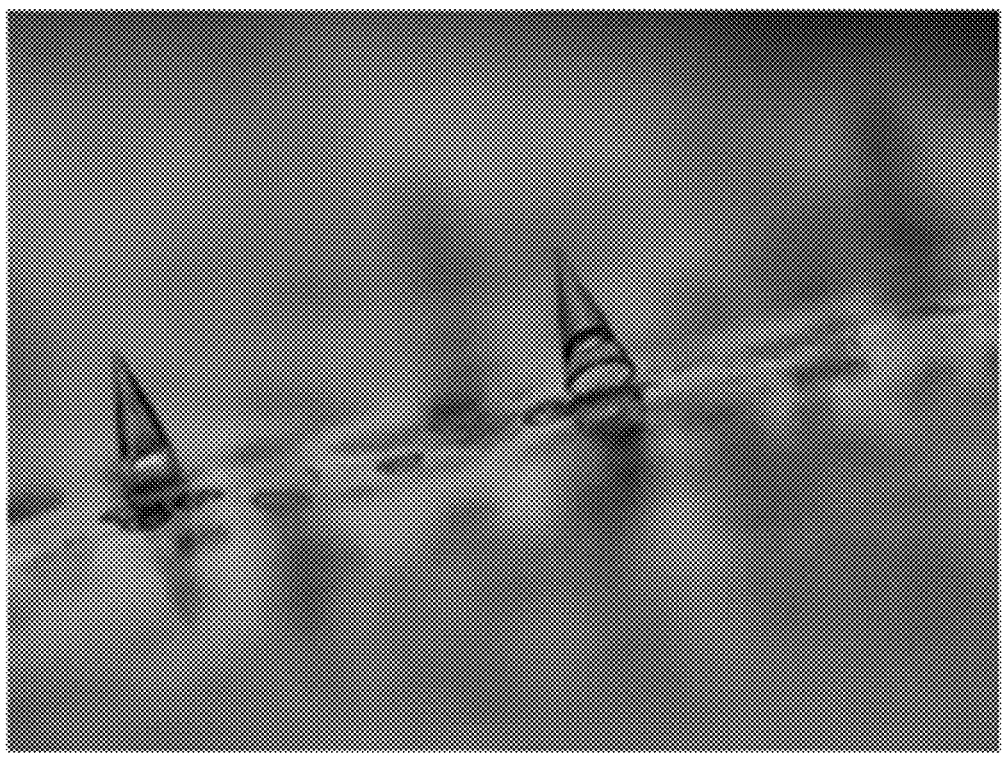
FIG. 5 shows images of microscopic observations of the microstructures produced when crosslinked hyaluronic acid hydrogels exceed the maximum viscosity range (Nikon Eclipse 80i, 80×).
Figure 5B:
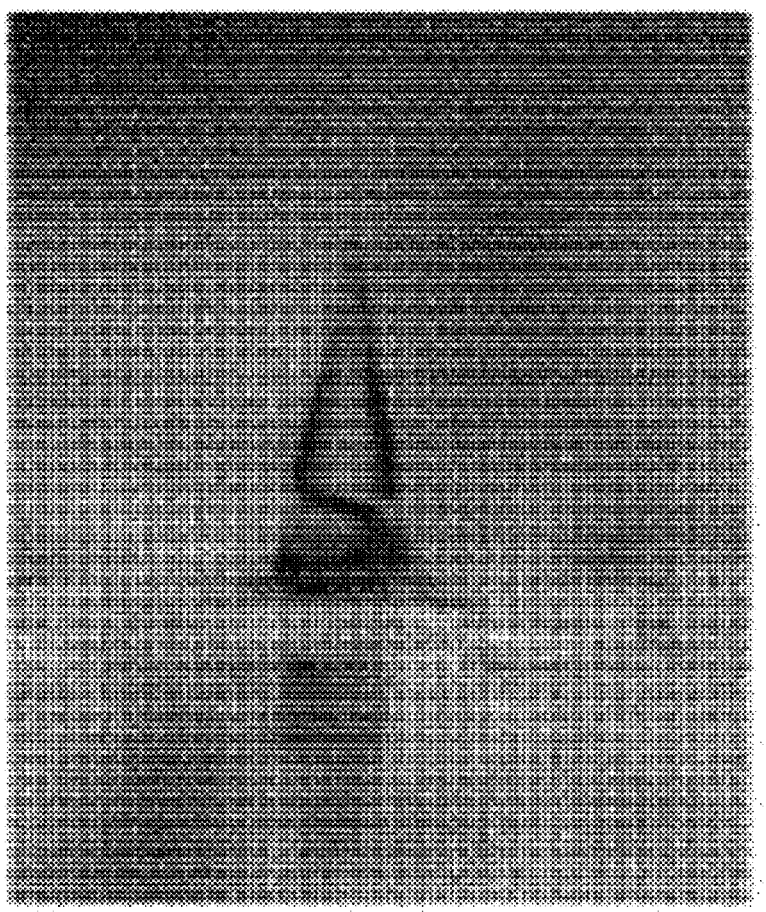

It was confirmed that, when the crosslinked hyaluronic acid hydrogel in Example 1-1-1 was prepared at the viscosity range of 2,500,000 cp according to Example 2-4, the crosslinked hyaluronic acid hydrogel could not be evenly injected into the mold, resulting in microstructures with empty insides or middle parts cut off (FIG. 5).

Example 6

Verification of the In-Vitro Degradation of Crosslinked Hyaluronic Acid Hydrogel (Hyaluronidase Assay)

To verify the inhibition of in-vitro degradation according to the process for preparing crosslinked hyaluronic acid hydrogels in the present invention, a degradation test was performed using the enzyme hydrolyzing hyaluronic acid on the products of Examples 1-1 through 1-7.

The inventors modified the method of Reissig et al. (a modified colorimetric method for the estimation of N-acetylamino sugar, J. Biol. Chem. 1955, 217:959-966) to perform a test of in-vitro degradation by the enzyme dissolving hyaluronic acid (hyaluronidase assay). The crosslinked hyaluronic acid hydrogels in Examples 1-1 through 1-7 were transferred to tubes at equal mass. Then, 0.2 M PBS (=pH 7.4) containing 500 U/mL of the hyaluronic acid hydrolyzing enzyme (hyaluronidase, Bovine Testes, Sigma-Aldrich, USA) was added. These mixtures were reacted at 37° C. for 6 hours and for 48 hours, respectively. Once the enzyme reaction stopped, 0.8M potassium borate (pH 9.1) was added to convert the N-acetyl glucosamine (NAG) degraded by the enzyme reaction into an intermediate, namely, glucoxazoline, and then it was heated for 5 minutes at 100° C. To measure the amount of N-acetyl glucosamine, which resulted from the degradation, the p-Dimethylaminobenzaldehyde color developing agent (DMAB) was added to the tube and the reaction took place for 30 minutes at 37° C. Then, among the crosslinking products degraded using supernatant after centrifugal separation (3,000 rpm, 10 minutes) was performed, the amount of NAG was measured using UV at an absorbance of 585 nm. Table 3 shows the relative effects of inhibiting biodegradation in the products of Examples 1-1 through 1-7 caused by the hyaluronic acid dissolving enzyme when the degradation rate of non-crosslinked hyaluronic acid was set to 100%.

TABLE 3

| | HA molecular weight (kDa) | Amount of crosslinking agent added (mole % per HA repeat unit) | Crosslinking rate (%) | Effect of inhibiting biodegradation (%) | |
|---|---|---|---|---|---|
| | | | | 6 hours | 48 hours |
| Comparative example (non-crosslinked HA) | 360 | — | — | 0 | 0 |
| Example 1-1-1 | 360 | 10 | 19.75 | 8.97 | 12.92 |
| Example 1-1-2 | 360 | 12 | 25.5 | 23.21 | 30.18 |
| Example 1-1-3 | 360 | 15 | 20.5 | 32.48 | 33.42 |
| Example 1-1-4 | 360 | 30 | 30.5 | 32.08 | 32.80 |
| Example 1-1-5 | 360 | 40 | 31.75 | 33.52 | 34.97 |
| Example 1-2-1 | 360 | 5 | 9.25 | 24.19 | 36.90 |
| Example 1-2-2 | 360 | 7.5 | 19.75 | 35.80 | 46.17 |
| Example 1-3 | 360 | 3 | 6.25 | 29.70 | 29.95 |
| Example 1-4 | 360 | 1 | 2.25 | 32.48 | 43.14 |
| Example 1-5-1 | 1,400 | 12 | 21.25 | 10.52 | 11.44 |
| Example 1-5-2 | 1,400 | 20 | 26.75 | 32.26 | 33.60 |
| Example 1-6 | 3,200 | 5 | 7.75 | 71.34 | 73.44 |
| Example 1-7 | 3,200 | 1 | 2.25 | 45.42 | 48.55 |

As shown in Table 3, the crosslinked hyaluronic acid hydrogels of Examples 1-1 through 1-7 exhibit the inhibitory effect of the hyaluronic acid dissolving enzyme present in the body and thereby longer duration in skin than non-crosslinked HA. Therefore, microstructures made using those crosslinked hyaluronic acid hydrogels provide long durations in the body and enhanced skin care benefits and enable the safe delivery of effective components in the body.

Example 7

Verification of In-Vitro Enzyme Degradation Rate (Half-life) of Microstructure Prepared Using Crosslinked Hyaluronic Acid Hydrogel To verify the differences in in-vitro enzyme degradation rate according to the method for preparing microstructures using crosslinked hyaluronic acid hydrogels, microstructures were made using the products of Examples 1-1 through 1-7 and the method of Example 2-2. The microstructures were then cut to a certain size and a hyaluronidase assay was performed. Then the times required for the microstructures to break down to 50% were compared.

The microstructures cut to certain sizes were transferred to respective tubes and then 0.2 M PBS (=pH 7.4) containing 16 units/mL of the hyaluronic acid dissolving enzyme (hyaluronidase, Bovine Testes, Sigma-Aldrich, USA) was added. These mixtures were reacted at 37° C., for 24 hours, 40 hours, 48 hours, 72 hours, 120 hours, 216 hours, and 360 hours, respectively. The enzyme reactions were stopped when respective reaction times ended, 0.8M potassium borate (pH 9.1) was added to convert the N-acetyl glucosamine (NAG) degraded by the enzyme reaction into an intermediate, namely, glucoxazoline, and then it was heated for 5 minutes at 100° C. To measure the amount of N-acetylglucosamine, which resulted from the degradation, the p-Dimethylaminobenzaldehyde color developing agent (DMAB) was added to the tube and the reaction took place for 30 minutes at 37° C. Then, among the crosslinking products degraded using supernatant after centrifugal separation (3,000 rpm, 10 minutes) was performed, the amount of NAG was measured using UV at an absorbance of 585 nm. The degradation rate of non-crosslinked hyaluronic acid was set to 100% and the degradation rate at each time by derivative was calculated to find the time required for the material to degrade to 50% (half-life). Table 4 shows the relative rate of biodegradation in the microstructures prepared using the products of Examples 1-1 through 1-7, which was caused by the hyaluronic acid dissolving enzyme, when the degradation rate of non-crosslinked hyaluronic acid was set to 100%.

TABLE 4

| Process for preparing microstructure | Crosslinked hyaluronic acid hydrogel | Amount of crosslinking agent added (mole % per HA repeat unit) | Crosslinking density (%) | Microstructure enzyme degradation rate Half-life (time) |
|---|---|---|---|---|
| Example 2-2 | Comparative example (non-crosslinked HA) | — | — | — |
| | Example 1-1-1 | 10 | 19.75 | 124 ± 13.0 |
| | Example 1-1-2 | 12 | 25.5 | 56 ± 9.0 |
| | Example 1-1-3 | 15 | 20.5 | 90 ± 10.0 |
| | Example 1-1-4 | 30 | 30.5 | 291 ± 65.6 |
| | Example 1-1-5 | 40 | 31.75 | 358 ± 14.3 |
| | Example 1-2-1 | 5 | 9.25 | 78 ± 16.9 |
| | Example 1-2-2 | 7.5 | 19.75 | 119 ± 14.6 |
| | Example 1-3 | 3 | 6.25 | 97 ± 18 |
| | Example 1-4 | 1 | 2.25 | 40 ± 10.0 |
| | Example 1-5-1 | 12 | 21.25 | 90 ± 7.5 |
| | Example 1-5-2 | 20 | 26.75 | 99 ± 4.7 |
| | Example 1-6 | 5 | 7.75 | 760 ± 33.2 |
| | Example 1-7 | 1 | 2.25 | 363 ± 15.5 |

Example 8

Testing of the Swelling Degree of Microstructure Prepared Using Crosslinked Hyaluronic Acid Hydrogel When water is added again after crosslinked hyaluronic acid hydrogels are dried, the hydrogels show high degrees of swelling. By limiting the range of swelling degrees during microstructure preparation, the absorption time and the drug delivery rate in the body can be adjusted.

In particular, the use of microstructures for skin insertion made using a material with high body absorption and swelling degree can produce great skin care results.

The crosslinked hyaluronic acid hydrogels that were completely dried for over six hours at the 70° C. dryer in Example 1 and the microstructures dried using the methods of Examples 2-1, 2-4 through 2-7, and 3-2 were cut to a certain size, submerged in water, and then kept at room temperature for 24 hours so that the microstructures could reach complete equilibrium. The swollen crosslinked HA hydrogels and structures were removed and free of surface water, and placed in the dryer after their weights were measured. Then after the moisture was completely removed, the weights of the dried crosslinked HA hydrogels and microstructures were measured to calculate the swelling degrees of the structures using the following formula:

$$\text{Swelling degree (\%)} = [(W_s - W_d)] / [(W_d)] \times 100(\%)$$

Ws: Weight of swollen microstructure, Wd: Weight of dried microstructure

TABLE 5

| Process for preparing micro-structure | Cross-linked hyaluronic acid hydrogel | Cross-linking density (%) | Homog-enized or not | Mix ratio (Cross-linked HA hydro-gel:Non-crosslinked HA) | Swelling degree (%) |
|---|---|---|---|---|---|
| — | Example 1-1-1 | 19.75 | − | — | 23250 |
| — | Example 1-1-2 | 25.5 | − | — | 66670 |
| — | Example 1-1-3 | 20.5 | − | — | 33210 |
| — | Example 1-1-4 | 30.5 | − | — | 58820 |
| — | Example 1-1-5 | 31.75 | − | — | 35710 |
| — | Example 1-2-1 | 9.25 | − | — | 13510 |
| — | Example 1-2-2 | 19.75 | − | — | 41660 |
| — | Example 1-3 | 6.25 | − | — | 39720 |
| — | Example 1-4 | 2.25 | − | — | 43210 |
| — | Example 1-5-1 | 21.25 | − | — | 29410 |
| — | Example 1-5-2 | 26.75 | − | — | 34480 |
| Example 2-1 | Example 1-3 | 6.25 | − | — | 37560 |
| Example 2-4 | Example 1-3 | 6.25 | − | — | 40200 |
| Example 2-5 | Example 1-3 | 6.25 | + | — | 69540 |
| Example 2-6 | Example 1-3 | 6.25 | + | — | 70110 |
| Example 2-7 | Example 1-1-1 | 19.75 | + | — | 3300 |
|  | Example 1-1-2 | 25.5 | + | — | 3050 |
|  | Example 1-1-3 | 20.5 | + | — | 2900 |
|  | Example 1-1-4 | 30.5 | + | — | 2370 |
|  | Example 1-1-5 | 31.75 | + | — | 2200 |
|  | Example 1-2-1 | 9.25 | + | — | 2330 |
|  | Example 1-2-2 | 19.75 | + | — | 2910 |
|  | Example 1-3 | 6.25 | + | — | 3730 |
|  | Example 1-4 | 2.25 | + | — | 4800 |

TABLE 5-continued

| Process for preparing micro-structure | Cross-linked hyaluronic acid hydrogel | Cross-linking density (%) | Homog-enized or not | Mix ratio (Cross-linked HA hydro-gel:Non-crosslinked HA) | Swelling degree (%) |
|---|---|---|---|---|---|
|  | Example 1-5-1 | 21.25 | + | — | 3710 |
|  | Example 1-5-2 | 26.75 | + | — | 3280 |
| Example 3-2 | Example 1-3 | 6.25 | + | 5:1 | 57840 |
|  |  |  |  | 1:1 | 38230 |
|  |  |  |  | 1:5 | 26220 |
|  |  |  |  | 1:10 | 11040 |

As shown in Table 5, the crosslinked hyaluronic acid hydrogels and microstructures in the present invention swell 20 to 400 times. After the homogenization process, they can even swell up to 700 times. Furthermore, when non-crosslinked hyaluronic acid is mixed in a certain ratio during microstructure preparation, the swelling degree can be adjusted.

Example 9

Testing to Maintain the Swelling Degree of Microstructure Prepared Using Crosslinked HA Hydrogel and Unmodified (Non-crosslinked) HA for Long Period (7 Days)

After the crosslinked hyaluronic acid hydrogels in Example 1 were homogenized and the crosslinked hyaluronic acid hydrogels and non-crosslinked HA were mixed in a weight ratio of 1:10 and microstructures were prepared using the method of Examples 3-1. Then, the degrees to which swelling is maintained from one to seven days were compared.

To test swelling degrees, microstructures prepared using the method in the Example above were cut to 10-20 mg/cm2. Then a cotton gauze or nonwoven wipe was placed flat on the flask and saline solution containing PBS or 0.003% methylene blue was added to soak the gauze or wipe completely. Then the microstructure samples were cut to an equal weight of 0.01 g and placed on the wet gauze or nonwoven wipe. The lid was placed on the flask to keep the gauze or wipe from drying up and stored in the 37° C. incubator. The swollen microstructures were weighed on the first, second, third, sixth, and seventh days to observe changes in the swelling degree.

The swelling degree was calculated using the formula shown in Example 8 and Table 6 shows the results.

TABLE 6

| Crosslinked hyaluronic acid hydrogel | Mix ratio (Crosslinked HA hydrogel:Non-crosslinked HA) | Process for preparing microstructure | Swelling degree (%) | | | | |
|---|---|---|---|---|---|---|---|
|  |  |  | Day 1 | Day 2 | Day 3 | Day 6 | Day 7 |
| Comparative example (Non-crosslinked HA hydrogel) | — | Example 2-2 | — | — | — | — | — |
| Example 1-1-1 | 1:10 | Example 3-1 | 9515 | 10592 | 8735 | 9518 | 9038 |
| Example 1-2-1 | 1:10 |  | 4936 | 5821 | 5403 | 4433 | 5062 |
| Example 1-3 | 1:10 |  | 6738 | 8192 | 6128 | 5638 | 6085 |

As shown in Table 6, the microstructure made using non-crosslinked hyaluronic acid alone did not show any swelling in saline solution, whereas the microstructure prepared according to Example 3-1 after mixing the HA hydrogel prepared according to Example 1 with non-crosslinked HA showed great swelling and remained swollen for seven days without any big change.

Figure 6:
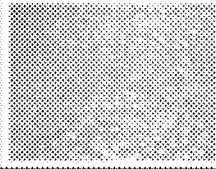
FIG. 6 represents the swollen gels of the microstructures produced using unmodified hyaluronic acid (non-crosslinked HA) and the microstructures produced by mixing crosslinked hyaluronic acid hydrogels and unmodified hyaluronic acid (non-crosslinked HA).

An observation of the shapes of the microstructures found that the microstructure made using non-crosslinked HA alone did not show any swelling in saline solution and dissolved completely with no shape, whereas the microstructure prepared according to Example 3-1 after mixing the HA hydrogel prepared according to Example 1 with non-crosslinked HA showed great swelling and remained swollen for seven days without any big change (FIG. 6).

Example 10

Figure 7A:
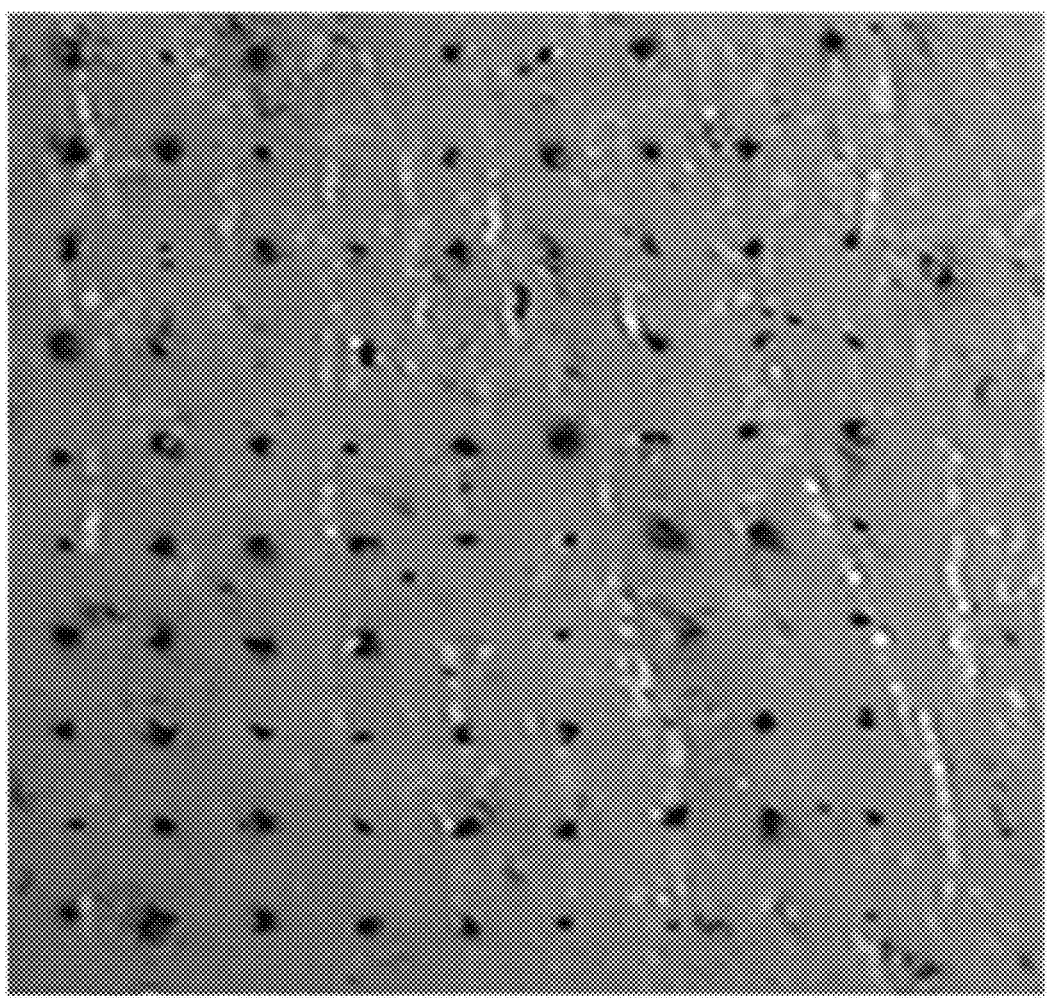
FIGS. 7a and 7b show the results of mechanical strength testing of the microstructures made using crosslinked hyaluronic acid hydrogels produced using the method of the present invention.
Figure 7B:
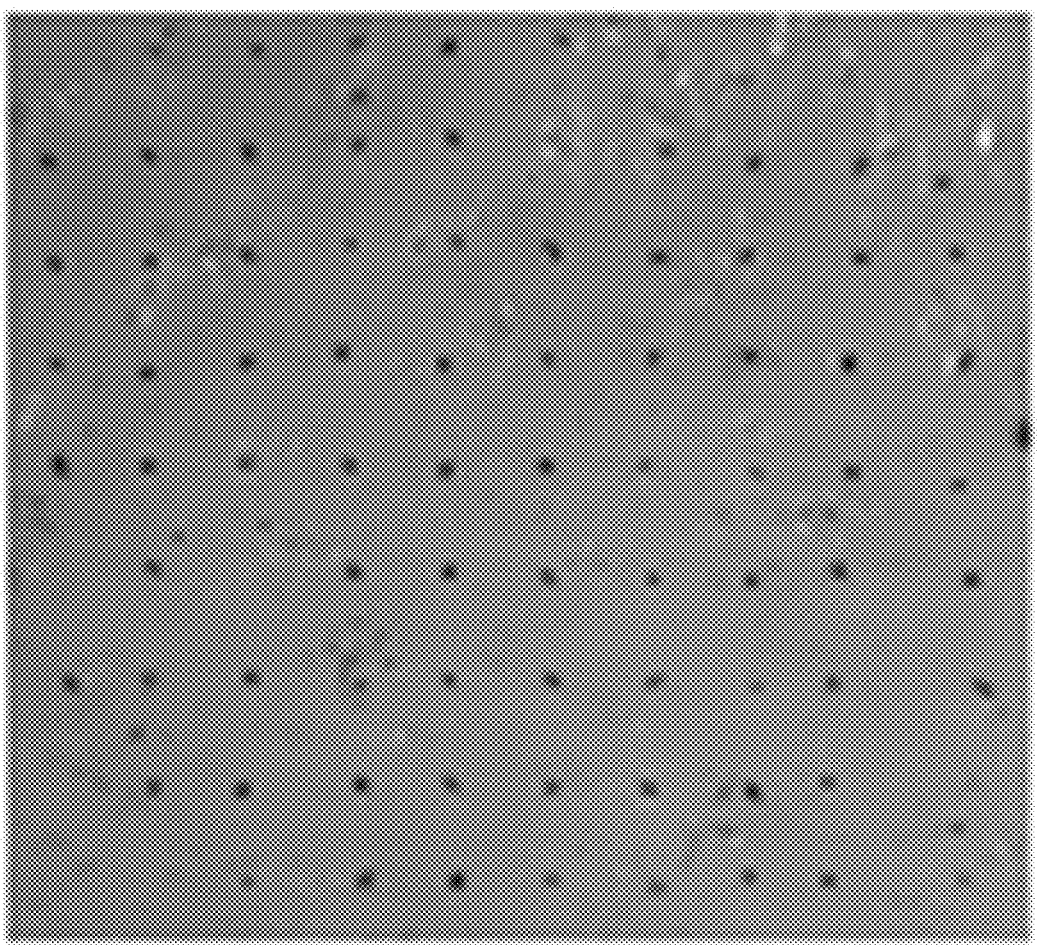

Testing to Verify the Penetration of Microstructure (Mechanical Strength of Microstructure) Prepared Using Crosslinked Hyaluronic Acid Hydrogel To check for any change in the mechanical strength of microneedles manufactured in Examples 2-4 and 2-5 using the crosslinked HA hydrogels of Example 1-1-3 and 1-4, the microstructures containing crosslinked HA hydrogels were applied to pig skin, dyed in trypan blue, and checked to determine whether or not they successfully formed holes in the skin. Consequently, the microneedles successfully created holes in the pig skin (FIGS. 7a and 7b). Therefore, since a microstructure containing crosslinked HA hydrogel provides sufficient mechanical strength to penetrate the skin, it can be concluded that they can efficiently deliver active ingredients in the skin.

Comparative Example 2

Lack of Enough Centrifugal Force Applied when Preparing Microstructure Using the Method of Example 2-3

Figure 8:
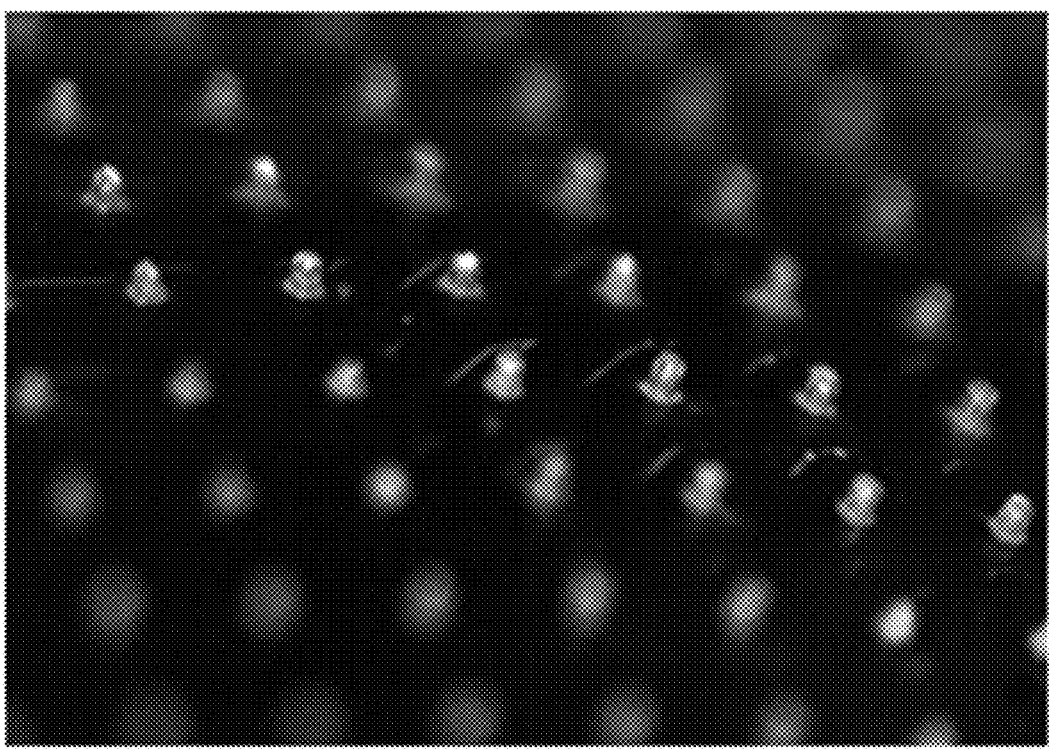
FIG. 8 shows a microscopic image (Nikon Eclipse 80i; 40×) of microstructures when the crosslinked hyaluronic acid hydrogel prepared by the present invention has not been injected with sufficient centrifugal force during microstructure preparation.

If the crosslinked HA hydrogel of Example 1-1-4 is prepared using the method of Example 2-3 while there is not enough centrifugal force (centrifugal separation for 5 minutes at 500 g), the lack of enough centrifugal force makes it impossible to supply the crosslinked HA hydrogel all the way into the mold, resulting in microstructures with blunt edges and heterogeneous shapes (FIG. 8).

Comparative Example 3

Lack of Sufficient Low-Pressure Injection when Preparing Microstructure Using the Method of Example 3-1

Figure 9:
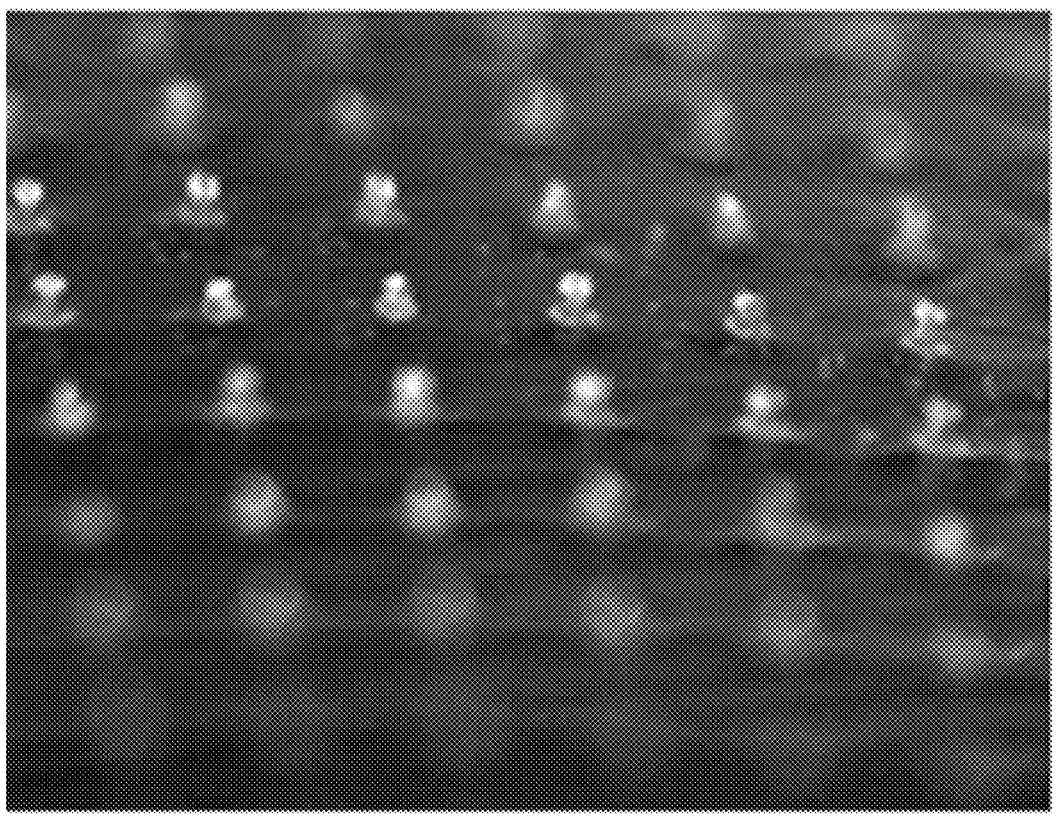
FIG. 9 shows a microscopic image (Nikon Eclipse 80i; 40×) of microstructures when the crosslinked hyaluronic acid hydrogel prepared by the present invention has not adequately been injected under depressurized conditions during microstructure preparation.

When microstructures are prepared using the method of Example 3-1 using a mixture of the crosslinked HA hydrogel of Example 1-1-5 and non-crosslinked HA (1:10), if the hydrogel is injected while low pressure is not sufficiently maintained (650 mmHg, low pressure injection for 3 minutes), then the mixture fails to be supplied all the way through, resulting in microstructures with blunt edges and heterogeneous lengths (FIG. 9).

Comparative Example 4

Lack of Sufficient Additional Drying when Preparing Microstructure Using the Method of Example 3-2

Figure 10A:
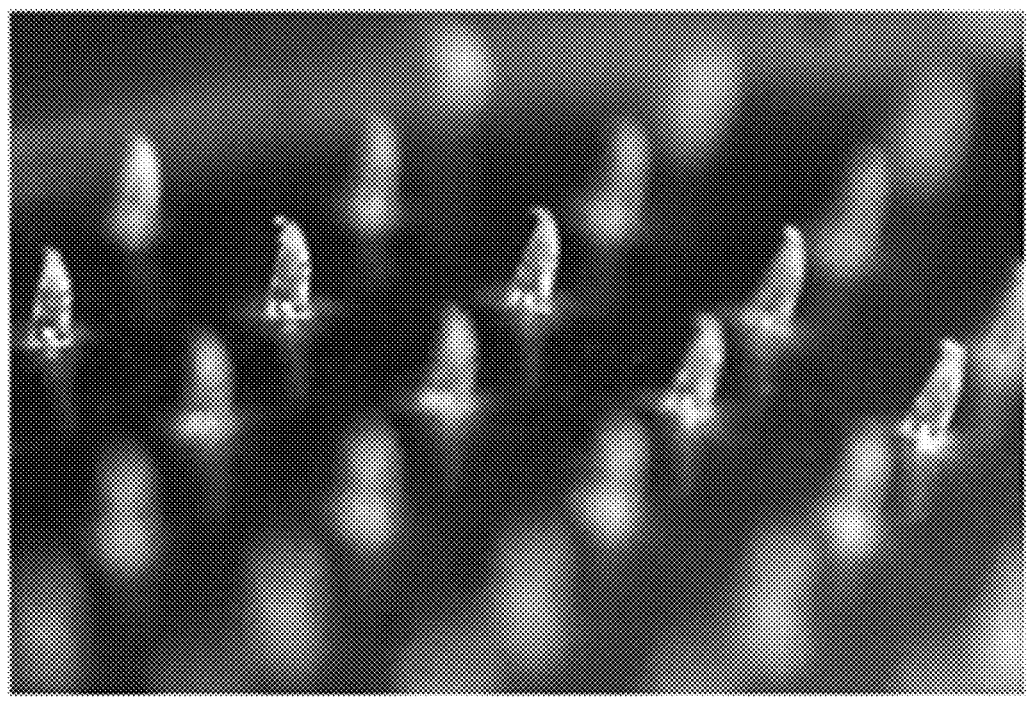
FIG. 10 shows microscopic images (Nikon Eclipse 80i; 40× (FIG. 10a); 80× (FIG. 10b)) of microstructures when the crosslinked hyaluronic acid hydrogel prepared by the present invention has not adequately been dried through an additional drying process during microstructure preparation.
Figure 10B:
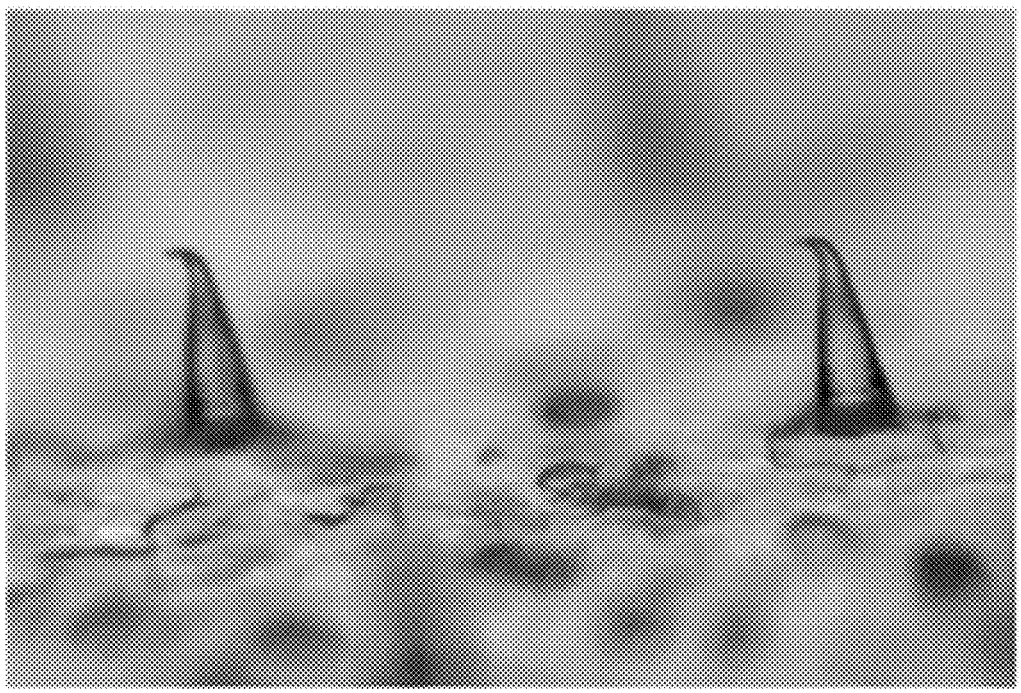

When microstructure is prepared using the method of Example 3-2 using a mixture of the crosslinked HA hydrogel of Example 1-1-2 and non-crosslinked HA (1:10), if there is no sufficient additional drying (additional drying for 5 minutes at 50° C.), the mixture fails to dry completely, resulting in the production of microstructures with bent edges (FIG. 10).

Although the present invention has been described in detail with reference to the specific features, it will be apparent to those skilled in the art that this description is only for a preferred embodiment and does not limit the scope of the present invention. Thus, the substantial scope of the present invention will be defined by the appended claims and equivalents thereof.

What is claimed is:

1. A microstructure formed from crosslinked hyaluronic acid hydrogels and non-crosslinked hyaluronic acid,
    wherein the microstructure provides mechanical properties appropriate for skin penetration and is selected from the group consisting of microneedle, microblade, microknife, microspike, microprobe, microbarb, microarray, and microelectrode, and
    wherein the weight ratio of the non-crosslinked hyaluronic acid to the crosslinked hyaluronic acid hydrogels is 1:1 to 10:1 and the solid content of the crosslinked hyaluronic acid hydrogels is equal to or below 15% (w/v) in the microstructure.

2. The microstructure of claim 1, wherein the crosslinked hyaluronic acid hydrogel has the crosslinking rate of 1-50%.

3. A method for preparing microstructures formed from crosslinked hyaluronic acid hydrogels and non-crosslinked hyaluronic acid comprising the following steps:
    (a) supplying a mixture of crosslinked hyaluronic acid hydrogel and non-crosslinked hyaluronic acid into a micro-mold;
    (b) injecting the mixture into the micro-mold cavities; and
    (c) separating the micro-mold and the mixture to form a microstructure,
    wherein the microstructure provides mechanical properties appropriate for skin penetration and is selected from the group consisting of microneedle, microblade, microknife, microspike, microprobe, microbarb, microarray, and microelectrode, and
    wherein the weight ratio of the non-crosslinked hyaluronic acid to the crosslinked hyaluronic acid hydrogels is 1:1 to 10:1 and the solid content of crosslinked hyaluronic acid hydrogels is equal to or below 15% (w/v) in the microstructure.

4. The method of claim 3, wherein the crosslinked hyaluronic acid hydrogel has a crosslinking density of 1-50%.

5. The method of claim 3, wherein the injection is carried out by applying an external force to the mixture.

6. The method of claim 5, wherein the external force is a centrifugal force.

7. The method of claim 3, wherein the injection is carried out at a pressure below atmospheric pressure.

8. The method of claim 7, wherein the pressure below atmospheric pressure is 100-750 mmHg.

9. The method of claim 3, wherein the method further comprises the step of drying the mixture after the step (a).

10. The method of claim 3, wherein the method further comprises the step of drying the mixture after the step (b).

11. The method of claim 3, wherein the method further comprises the step of drying the mixture before the step (a).

12. The method of claim 9, wherein the drying is carried out for 10 minutes to 60 hours at 15 to 90° C.

13. The method of claim 9, wherein the drying is carried out at a pressure below atmospheric pressure.

14. The method of claim 3, wherein the method comprises the step of homogenizing the crosslinked hyaluronic acid hydrogel before the step (a).

15. The method of claim 3, wherein the crosslinked hyaluronic acid hydrogel is crosslinked by an ether crosslinking agent.

16. The method of claim 3, wherein the crosslinked hyaluronic acid hydrogel is crosslinked by a 1,4butanediol diglycidyl ether.

* * * * *